(12) United States Patent
Chen et al.

(10) Patent No.: US 6,847,898 B1
(45) Date of Patent: Jan. 25, 2005

(54) REAL TIME DETERMINATION OF GAS SOLUBILITY AND RELATED PARAMETERS IN MANUFACTURING PROCESSES

(75) Inventors: Qingyuan Chen, Appleton, WI (US); Robert Josef Franda, Sherwood, WI (US)

(73) Assignee: Appleton Papers Inc., Appleton, WI (US)

( * ) Notice: Subject to any disclaimer, the term of this patent is extended or adjusted under 35 U.S.C. 154(b) by 0 days.

(21) Appl. No.: 10/644,997

(22) Filed: Aug. 21, 2003

(51) Int. Cl.[7] .......................... G01N 31/00; G06F 19/00
(52) U.S. Cl. ............................ 702/24; 702/22; 702/23; 702/25; 702/137
(58) Field of Search ............................ 702/22, 23, 24, 702/25, 98, 99, 137; 73/19.01, 53.01; 700/265, 266

(56) References Cited

U.S. PATENT DOCUMENTS

| | | | |
|---|---|---|---|
| 5,041,990 A | * | 8/1991 | Yabumoto et al. ............ 702/24 |
| 5,365,435 A | | 11/1994 | Stephenson ................. 364/420 |
| 6,496,781 B1 | | 12/2002 | Chen et al. .................... 702/25 |
| 6,766,680 B2 | * | 7/2004 | Chen et al. ................. 73/19.05 |

OTHER PUBLICATIONS

Bergman et al., "On–Line Measurement of Coating Color Quality in Coater Supply System", 1999 TAPPI Coating Conference, Toronto, Canada, 1999 (16 pages).
Mütek News, No. 7, Aug. 2001 (4 pages).
Pulse) ) ) ) ) Air_V3, www.papec.com, Dec. 21, 2001 (3 pages).
Anton Paar, "On–line CO2 measurement in the beer and soft drink industry", Press Release, Jul. 2001 (3 pages).

* cited by examiner

*Primary Examiner*—Bryan Bui
(74) *Attorney, Agent, or Firm*—Birch, Stewart, Kolasch & Birch, LLP

(57) ABSTRACT

Methods and apparatuses for determining entrained and/or dissolved gas content of gas-liquid mixtures. Data generated is used to control the True (air-free) or Apparent (air-containing) Density or Entrained Air content of liquids within optimum ranges, e.g. in paper coating processes and in the manufacture of food products, personal care products, pharmaceutical products, paints, petroleum blends, etc. For example, an indirect method of continuously determining the amount of gas entrained in a liquid, by: continuously measuring the temperature, flow rate, and apparent density of the mixture at two different pressure states, and calculating the volume percentage of the gas in the liquid by using equation (28)

$$x\% = \frac{V_s}{V_s + V} \quad (28)$$

wherein V is the volume of the gas-free liquid calculated by equation (23)

$$V = \frac{1}{\rho_1} - \left[ \frac{P_2}{P_2 - P_1}\left(\frac{1}{\rho_1} - \frac{1}{\rho_2}\right) - \frac{RT}{P_2 - P_1} g\left(\frac{\Delta P}{Q^a}\right) \right] \quad (23)$$

in which $P_1$ and $P_2$ are two different ambient pressures and $\Delta P = P_2 - P_1$, $\rho_1$ and $\rho_2$ are apparent densities of the liquid sample measured at $P_1$ and $P_2$, respectively, R is the constant of the Ideal Gas Law, T is the liquid temperature, Q is the flow rate, $g(\Delta P/Q^a)$ is a function for determining the amount of gas being dissolved between $P_2$ and $P_1$, and $V_s$ is determined by equation (27)

$$V_s = \frac{T_s}{T} \frac{P_1 P_2}{P_s(P_2 - P_1)}\left(\frac{1}{\rho_1} - \frac{1}{\rho_2}\right) - \frac{RT_s}{P_s}\left(\frac{P_1}{P_2 - P_1} g\left(\frac{\Delta P}{Q^a}\right) - g\left(\frac{P_1 - P_s}{Q^a}\right)\right). \quad (27)$$

24 Claims, 9 Drawing Sheets

REAL TIME DETERMINATION OF GAS SOLUBILITY AND RELATED PARAMETERS IN MANUFACTURING PROCESSES

FIELD OF THE INVENTION

This invention provides means for improving control of continuous processes that handle liquids, and therefore provides benefits to manufacturers by enabling them to effectively monitor and operate their processes. Data generated by this invention can be used to control the True (air-free) or Apparent (air-containing) Density or Entrained Air content of liquids within optimum ranges, for instance in paper coating processes and in the manufacture of such products as food products (ketchup, mayonnaise, ice cream, syrup), carbonated beverages, personal care products (skin cream, shampoo), pharmaceutical products, paints, petroleum blends, and the like. This invention is useful in any industry where information pertaining to liquid density or entrained air and other gases is employed to optimize industrial processing.

BACKGROUND OF THE INVENTION

Those skilled in the arts of processing liquids desire to know how much air and/or other gases are entrapped and dissolved therein for a variety of reasons. Entrapped air can cause undesired foaming during processing, e.g. in papermaking and in the preparation of foodstuffs, and can result in disruption of film products, e.g. from paints. Entrained gases distort such processing parameters as density, making precise control of processes impossible. U.S. Pat. No. 5,365,435 illustrates the utilization of slurry density determination in fluid processing at an oil well site.

Those skilled in the art know that, generally, the more viscous a fluid being processed, the more difficult it is for any entrained air to escape from it and consequently the greater the amount of air bubbles likely to be accumulated therein. Also, as pressure on a fluid is lowered or temperature of a fluid is raised, dissolved air or other gas therein tends to leave solution and form bubbles in the fluid.

There are a number of instruments that are currently commercially available for measuring the air or gas content in a liquid. Such instruments include Metso's COLORMAT, Mütek's GAS-60, BTG's CCA 3000, Papec's PULSE)))) AIR, Capella Technology's CAPTAIR, Anton-Paar's CARBO 2100 $CO_2$ analyzer, and CyberMetrics' AIR TESTER.

Mütek's GAS-60, for instance, is said to be useful in the context of minimizing pinholes (voids) in papermaking processes. Pinholes develop when pressure is reduced and dissolved gases—which accumulate in the papermaking process due to mechanical effects and chemical and biological reactions~are released. The GAS 60 is installed on line and is used to determine the gas content of entrained and dissolved gases in pulp suspensions. Having determined gas content, process engineers are able to calculate how much (expensive) deaerating additive should be used, and thus to avoid unnecessarily increased manufacturing costs due to employing too much deaerating additive.

Papec's PULSE))))AIR_V3 is a sensor for the measurement of entrained air and gases in process fluids. It is said to be useful in the pulp and paper industry in connection with machine headboxes and white water systems, coatings, and brownstock washers, in the secondary fiber industry (for effluent treatment), in the paint industry, in oil bottling processes, in the processing of well drilling muds, and in general in any application needing entrained air information.

Anton-Paar's CARBO 2100 $CO_2$ analyzer employs a patented impeller method which is said to make it significantly faster that other commercially available systems for measuring and monitoring tasks and also for regulating the $CO_2$ content of process liquids during production runs in the beer and soft drink industry.

It is believed that all of these instruments adopt a common approach, using Boyle's Law. Boyle's law is given by the equation $$P_1V_1 = P_2V_2 \quad (1)$$

where $V_1$ and $V_2$ are the volumes of the entrained gas in the liquid at two different pressures, $P_1$ and $P_2$, respectively. This common approach measures the volume difference $\Delta V = V_1 - V_2$ between $P_1$ and $P_2$, and calculates the volumes of entrained gas, $V_1$ and $V_2$, from Boyle's Law as $$V_1 = \frac{P_2 \Delta V}{P_2 - P_1} \text{ and } V_2 = \frac{P_1 \Delta V}{P_2 - P_1}. \quad (2)$$

More general formulas, which correlate the volumes of entrained gas with the pressures being acted upon, can be derived from the Ideal Gas Law as $$P_1V_1 = n_1 RT_1 \quad (3)$$

and $$P_2V_2 = n_2 RT_2 \quad (4)$$

where R is the gas constant, and $n_1$, $T_1$ and $n_2$, $T_2$ are moles of entrained gas and temperatures at $P_1$ and $P_2$, respectively. In the case of $n_1 = n_2$ and $T_1 = T_2$, equations (3) and (4) can be simplified to the equation of Boyle's Law given in (1). Hence, Boyle's Law is, in fact, a special case of the Ideal Gas Law and is valid only if the moles of entrained gas and temperatures at $P_1$ and $P_2$ are kept constant.

Incidentally, $\Delta V$—that is, change in volume—can be determined either by directly measuring volumes and/or changes in volume or indirectly by measuring changes in apparent density.

In practice, a portion of the gas in a fluid will be dissolved in that fluid. At equilibrium, the solubility of gas is, as a general rule, proportional to the gas pressure as stated in Henry's Law $$P = Hn_d \quad (5)$$

where P, H, $n_d$ are the pressure of the gas being dissolved, the constant of Henry's Law, and moles of dissolved gas, respectively. This unquestionably makes $n_1 \neq n_2$ between two different pressures, $P_1$ and $P_2$, causing a violation of Boyle's Law.

Therefore, using Boyle's Law for gas-liquid mixtures, in which the occurrence of gas dissolving/exsolving is inevitable, is only an approximation of the Ideal Gas Law. The accuracy of such an approximation is directly affected by the amount of dissolved/exsolved gas. This means that using Boyle's Law in the traditional approach, where the measurements are usually taken at two equilibrium states as commonly practiced in the prior art, would maximize the error for entrained gas calculation since the amount of dissolved/exsolved gas would be maximized between the two equilibrium measurement points.

To cure this error, there have been some attempts to use Henry's Law to compensate for the amount of the dissolved gas. This approach, however, is generally impractical, inasmuch as the constants of Henry's Law are not available for many process liquids, particularly for those containing multiple-components such as coating slurries. Using the known constant of one liquid to approximate the constant of the others may potentially introduce a considerable amount of error, because the solubility of gases such as air changes dramatically from liquid to liquid. The solubility of air in isooctane at standard temperature and pressure, for example, is more than 100 times higher than the solubility of air in water.

The present inventors had previously developed a method for the improved control of continuous processes that handle liquids, which method is disclosed in U.S. patent application Ser. No. 10/046,240 (filed Jan. 16, 2002). In that method, the amount of gas in a liquid is determined by subjecting a mixture of an incompressible liquid sample and a compressible gas to three or more different equilibrium pressure states, measuring the temperature and volume of the mixture at each of the pressure states, determining the changes in volume of the mixture between at least two different pairs of pressure states, and calculating the amount of gas in the liquid sample.

SUMMARY OF THE INVENTION

The present invention provides methods and apparatuses for determining the entrained gas content and/or the dissolved gas content of a gas-liquid mixture. This invention provides means for improving control of continuous processes that handle these mixtures, and therefore provides benefits to manufacturers by enabling them to effectively monitor and operate their processes. Data generated by this invention can be used for instance to control the True (air-free) or Apparent (air-containing) Density or Entrained Air content of liquids within optimum ranges, for instance in paper coating processes and in the manufacture of such products as food products (ketchup, mayonnaise, ice cream, syrup), personal care products (skin cream, shampoo), pharmaceutical products, paints, petroleum blends, and the like. This invention is useful in any industry where information on entrained and or dissolved gas, and related parameters such as true density and solubility of process liquids, is employed.

This invention consists of methods and apparatuses for measuring entrained and dissolved gas content that is an improvement over prior art. Data generated by this invention minimizes the measurement error caused by the dissolving or exsolving of gases with changes in pressure of a fluid, while providing instantaneous measurement. This is accomplished through apparatuses that measure system conditions at each of two pressure states within a very short period of time. Methods are also defined herein which constitute improvements over the traditional approach.

DIRECT AND INDIRECT MEASUREMENT METHODS. More specifically, the present invention provides indirect and direct measurement methods, as follows:

An indirect method of determining the amount of gas entrained in a liquid in a batch (static) mode, by: subjecting a mixture of an incompressible liquid sample and a compressible gas to two different pressure states, measuring the temperature and apparent density of the mixture at each of the two pressure states, and calculating the volume percentage of said gas in said liquid sample by using equation (28)

$$x\% = \frac{V_s}{V_s + V} \quad (28)$$

wherein $V_S$ is determined by equation (33)

$$V_s = \frac{T_s}{T} \frac{P_1 P_2}{P_s(P_2 - P_1)} \left( \frac{1}{\rho_1} - \frac{1}{\rho_2} \right) - \frac{RT_s}{C} \quad [33]$$

in which $P_1$ and $P_2$ are two different ambient pressures, $\rho_1$ and $\rho_2$ are apparent densities of the liquid sample measured at $P_1$ and $P_2$, respectively, $P_s$ and $T_s$ are standard pressure (1 atm) and temperature (0° C.), R is the constant of the Ideal Gas Law, T is the temperature of the liquid sample, and C is the gas solubility coefficient at a static state; and V is the volume of the gas-free liquid calculated through equation (32)

$$V = \frac{1}{\rho_1} - \left[ \frac{P_2}{P_2 - P_1} \left( \frac{1}{\rho_1} - \frac{1}{\rho_2} \right) - \frac{RT}{C} \right]. \quad [32]$$

An indirect method of continuously determining the amount of gas entrained in a liquid in a dynamic mode, by: continuously measuring the temperature, flow rate, and apparent density of the mixture at two different pressure states, and calculating the volume percentage of said gas in said liquid by using equation (28)

$$x\% = \frac{V_s}{V_s + V} \quad (28)$$

wherein V is the volume of the gas-free liquid calculated by equation (23)

$$V = \frac{1}{\rho_1} - \left[ \frac{P_2}{P_2 - P_1} \left( \frac{1}{\rho_1} - \frac{1}{\rho_2} \right) - \frac{RT}{P_2 - P_1} g\left(\frac{\Delta P}{Q^a}\right) \right] \quad (23)$$

in which $P_1$ and $P_2$ are two different ambient pressures and $\Delta P = P_2 - P_1$, $\rho_1$ and $\rho_2$ are apparent densities of the liquid sample measured at $P_1$ and $P_2$, respectively, R is the constant of the Ideal Gas Law, T is the liquid temperature, Q is the flow rate, and $g(\Delta P/Q^a)$ is a function through which the gas solubility coefficients at a dynamic state are determined; and $V_s$ is determined by equation (27)

$$V_s = \frac{T_s}{T} \frac{P_1 P_2}{P_s(P_2 - P_1)} \left( \frac{1}{\rho_1} - \frac{1}{\rho_2} \right) - \frac{RT_s}{P_s} \left( \frac{P_1}{P_2 - P_1} g\left(\frac{\Delta P}{Q^a}\right) - g\left(\frac{P_1 - P_s}{Q^a}\right) \right). \quad (27)$$

in which $P_s$ and $T_s$ are standard pressure (1 atm) and temperature (0° C.), and $$g\left(\frac{P_1 - P_s}{Q^a}\right)$$

is a function for determining the amount of gas being dissolved between $P_1$ and $P_s$.

An indirect method of determining the air-free density of a liquid at a static state, by: subjecting a mixture of an incompressible liquid sample and a compressible gas to two different pressure states, measuring the temperature and apparent density of the mixture at each of the two pressure states, and calculating the true density of said liquid sample by using equation (24)

$$\rho = \frac{1}{V} \quad (24)$$

wherein V is the volume of the gas-free liquid as determined by equation (32)

$$V = \frac{1}{\rho_1} - \left[\frac{P_2}{P_2 - P_1}\left(\frac{1}{\rho_1} - \frac{1}{\rho_2}\right) - \frac{RT}{C}\right] \quad [32]$$

in which $P_1$ and $P_2$ are two different ambient pressures, $\rho_1$ and $\rho_2$ are apparent densities of the liquid sample measured at $P_1$ and $P_2$, respectively, R is the constant of the Ideal Gas Law, T is the temperature of the liquid sample, and C is the gas solubility coefficient at a static state.

An indirect method of determining the air-free density of a liquid at a dynamic state, by: measuring two different apparent densities of the mixture and two corresponding ambient pressures at which the apparent densities are determined, measuring the temperature and flow rate, and calculating the true density of said liquid sample by using equation (24)

$$\rho = \frac{1}{V} \quad (24)$$

wherein V is the volume of the gas-free liquid as determined by equation (23)

$$V = \frac{1}{\rho_1} - \left[\frac{P_2}{P_2 - P_1}\left(\frac{1}{\rho_1} - \frac{1}{\rho_2}\right) - \frac{RT}{P_2 - P_1}g\left(\frac{\Delta P}{Q^a}\right)\right] \quad [23]$$

in which $P_1$ and $P_2$ are two different ambient pressures and $\Delta P = P_2 - P_1$, $\rho_1$ and $\rho_2$ are apparent densities of the liquid sample measured at $P_1$ and $P_2$, respectively, R is the constant of the Ideal Gas Law, T is the temperature of the liquid sample, and $$g\left(\frac{\Delta P}{Q^a}\right)$$

is the gas solubility function.

An indirect method for determining the gas solubility coefficient for a certain gas-liquid mixture at a dynamic state, by: subjecting said gas-liquid mixture to flow at several different flow rates, $Q_1, Q_2, \ldots, Q_i$; measuring two different apparent densities of the mixture and two related ambient pressures at which the apparent densities are determined at each of the flow rates; acquiring off-line the true, gas-free liquid density, $\rho^*$, through one-time measurement; determining the gas solubility coefficients, $A_0, A_1, A_2, \ldots, A_i$, by solving a group of linear equations (19)

$$A_0 + A_1\left(\frac{\Delta P}{Q^a}\right) + A_2\left(\frac{\Delta P}{Q^a}\right)^2 + \ldots + A_i\left(\frac{\Delta P}{Q^a}\right)^i = S_1\bigg|_{Q=Q_1} \quad (19)$$

$$A_0 + A_1\left(\frac{\Delta P}{Q^a}\right) + A_2\left(\frac{\Delta P}{Q^a}\right)^2 + \ldots + A_i\left(\frac{\Delta P}{Q^a}\right)^i = S_2\bigg|_{Q=Q_2}$$

$$A_0 + A_1\left(\frac{\Delta P}{Q^a}\right) + A_2\left(\frac{\Delta P}{Q^a}\right)^2 + \ldots + A_i\left(\frac{\Delta P}{Q^a}\right)^i = S_i\bigg|_{Q=Q_i}$$

in which $Q_1, Q_2, \ldots, Q_i$ are the different flow rates generated for obtaining the gas solubility coefficients at a dynamic state, $\Delta P$ is the difference of the said two ambient pressures at each of the flow rates, a is an index reflecting the weak influence of flow rate on gas solubility, and $S_1, S_2, \ldots, S_i$ are intermediate variables determined by equation (20)

$$S_1 = \frac{1}{RT}\left[P_I\left(\frac{1}{\rho_I} - \frac{1}{\rho^*}\right) - P_{II}\left(\frac{1}{\rho_{II}} - \frac{1}{\rho^*}\right)\right]\bigg|_{Q=Q_1} \quad (20)$$

$$S_2 = \frac{1}{RT}\left[P_I\left(\frac{1}{\rho_I} - \frac{1}{\rho^*}\right) - P_{II}\left(\frac{1}{\rho_{II}} - \frac{1}{\rho^*}\right)\right]\bigg|_{Q=Q_2}$$

$$\ldots$$

$$S_i = \frac{1}{RT}\left[P_I\left(\frac{1}{\rho_I} - \frac{1}{\rho^*}\right) - P_{II}\left(\frac{1}{\rho_{II}} - \frac{1}{\rho^*}\right)\right]\bigg|_{Q=Q_i}$$

in which $P_I$ and $P_{II}$ are two different ambient pressures measured at each of the flow rates, $\rho_I$ and $\rho_{II}$ are apparent densities of the gas-liquid mixture measured at $P_I$ and $P_{II}$, respectively, R is the constant of the Ideal Gas Law, T is the liquid temperature, Q is the flow rate, and $\rho^*$ is the predetermined gas-free liquid density as defined above; attaining the gas solubility function $$g\left(\frac{\Delta P}{Q^a}\right) = A_0 + A_1\left(\frac{\Delta P}{Q^a}\right) + A_2\left(\frac{\Delta P}{Q^a}\right)^2 + \ldots + A_i\left(\frac{\Delta P}{Q^a}\right)^i$$

upon the solution of the gas solubility coefficients, $A_0, A_1, A_2, \ldots, A_i$.

An indirect method for determining the gas solubility coefficient for a certain gas-liquid mixture at a static state, by: measuring two different apparent densities of the mixture and two related ambient pressures at which the apparent densities are determined; acquiring off-line the true, gas-free liquid density, $\rho^*$, through one-time measurement; determining the gas solubility coefficients, C, at a static state by solving equation (30)

$$C = RT(P_{II} - P_I)\left[P_I\left(\frac{1}{\rho_I} - \frac{1}{\rho^*}\right) - P_{II}\left(\frac{1}{\rho_{II}} - \frac{1}{\rho^*}\right)\right]^{-1} \quad (30)$$

in which $P_I$ and $P_{II}$ are two different ambient pressures, $\rho_I$ and $\rho_{II}$ are apparent densities of the gas-liquid mixture measured at $P_I$ and $P_{II}$, respectively, R is the constant of the Ideal Gas Law, T is the liquid temperature, and $\rho^*$ is the predetermined gas-free liquid density as defined above.

In all of the above indirect measurement methods, the two pressure states differ from one another by at least 1 psi, preferably by at least 1 atmosphere. Similarly, the two pressure states differ from one another at least to the extent that the two different apparent densities of said liquid differ from one another by at least 0.2%, preferably by at least 0.5%.

A direct method of determining the amount of gas entrained in a liquid, by: subjecting a mixture of an incompressible liquid sample and a compressible gas to two different pressure states, measuring the temperature and volume of the mixture at each of the two pressure states, determining the changes in volume of the mixture between the two pressure states, and calculating the volume percentage of said gas in said liquid sample by using equation (28)

$$x\% = \frac{V_s}{V_s + V} \quad (28)$$

wherein $V_s$ is determined by equation (37)

$$V_s = \frac{T_s}{T} \frac{P_1 P_2 \Delta V}{P_s(P_2 - P_1)} - \frac{RT_s}{C} \quad [37]$$

in which $T_s$ is 0° C., $P_1$ and $P_2$ are two different ambient pressures, $\Delta V$ is the volume difference of the gas-liquid mixture in a sample chamber between $P_1$ and $P_2$, R is the constant of the Ideal Gas Law, T is the temperature of the liquid sample (ambient temperature), $P_s$ is 1 atm, and C is the gas solubility coefficient at a static state; and V is the volume of the gas-free liquid in the sample chamber determined by equation (36)

$$V = V_{tI} - \left[ \frac{P_2 \Delta V}{P_2 - P_1} - \frac{RT}{C} \right] \quad (36)$$

in which $V_{t1}$ is the volume of the gas-liquid mixture in the sample chamber at $P_1$.

A direct method of determining the air-free density of a liquid, by: subjecting a mixture of an incompressible liquid sample and a compressible gas to two different pressure states, measuring the temperature and volume of the mixture at each of the two pressure states, determining the changes in volume of the mixture between the two pressure states, and calculating the true density of said liquid sample by using equation (24)

$$\rho = \frac{1}{V} \quad (24)$$

wherein V is the volume of the gas-free liquid measured as determined by equation (36)

$$V = V_{tI} - \left[ \frac{P_2 \Delta V}{P_2 - P_1} - \frac{RT}{C} \right] \quad [36]$$

in which $P_1$ and $P_2$ are two different ambient pressures, $V_{t1}$ is the volume of gas-liquid mixture in the sample chamber at $P_1$, $\Delta V$ is the change in volume of gas-liquid mixture in the sample chamber between $P_1$ and $P_2$, R is the constant of the Ideal Gas Law, T is the temperature of the liquid sample, and C is the gas solubility coefficient at a static state.

A direct method for determining the gas solubility coefficient for a gas-liquid mixture at a static state, by: subjecting a mixture of an incompressible liquid sample and a compressible gas to a sample chamber; compressing or expanding the sample chamber and measuring the volume of gas-liquid mixture, $V_{t1}$, at the first pressure state, $P_I$; compressing or expanding the sample chamber further and measuring the volume of gas-liquid mixture, $V_{tII}$, at the second pressure state, $P_{II}$; measuring the volume of gas-free liquid in the sample chamber V, by adding degassing chemicals, by allowing the sample to sit for a time sufficiently long to dissipate all of the free gas bubbles, or by increasing the pressure of the sample chamber excessively to dissolve all of the free gas; calculating the volumes of the free gas, $V_I$ and $V_{II}$ at $P_1$ and $P_{11}$ respectively, $V_I = V_{tI} - V$ and $V_{II} = V_{tII} - V$; determining the gas solubility coefficient, C, by using equation (34)

$$C = \frac{RT(P_{II} - P_I)}{P_I V_I - P_{II} V_{II}} \quad (34)$$

in which $P_I$ and $P_{II}$ are two different ambient pressures, $V_I$ and $V_{II}$ are volumes of the gas-liquid mixture in the sample chamber measured at $P_I$ and $P_{II}$, respectively, R is the constant of the Ideal Gas Law, T is the liquid temperature.

In all of the above direct measurement methods, the two pressure states differ from one another by at least 1 psi, preferably by at least 1 atmosphere. Similarly, the two pressure states differ from one another at least to the extent that the two different volumes of said liquid differ from one another by at least 0.2%, preferably by at least 0.5%.

INDUSTRIAL PROCESS CONTROL. The indirect and direct measurement methods of this invention can be used in industrial process control, for instance as follows:

In a method for automatically controlling the output of a continuous process with a liquid carrier that contains one or more gases, by: setting a quantitative target for volume-% of one or more gases in the liquid carrier; calculating the volume percentage of said gas in said liquid sample by using equation (28)

$$x\% = \frac{V_s}{V_s + V} \quad (28)$$

wherein V is the volume of the gas-free liquid calculated by equation (23)

$$V = \frac{1}{\rho_1} - \left[ \frac{P_2}{P_2 - P_1} \left( \frac{1}{\rho_1} - \frac{1}{\rho_2} \right) - \frac{RT}{P_2 - P_1} g\left( \frac{\Delta P}{Q^a} \right) \right] \quad (23)$$

in which $P_1$ and $P_2$ are two different ambient pressures and $\Delta P = P_2 - P_1$, $\rho_1$ and $\rho_2$ are apparent densities of the liquid sample measured at $P_1$ and $P_2$, respectively, R is the constant of the Ideal Gas Law, T is the liquid temperature, Q is the flow rate, and $g(\Delta P/Q^a)$ is a function through which the gas solubility coefficients at a dynamic state are determined; and $V_s$ is determined by equation (27)

$$V_s = \frac{T_s}{T} \frac{P_1 P_2}{P_s(P_2 - P_1)} \left( \frac{1}{\rho_1} - \frac{1}{\rho_2} \right) - \frac{RT_s}{P_s} \left( \frac{P_1}{P_2 - P_1} g\left( \frac{\Delta P}{Q^a} \right) - g\left( \frac{P_1 - P_s}{Q^a} \right) \right) \quad (27)$$

in which $P_s$ and $T_s$ are standard pressure (1 atm) and temperature (0° C.), $P_1$, $P_2$, $P_s$, $\Delta P$, $\rho_1$, $\rho_2$, R, Q, and T are the same as defined in this claim, and $$g\left( \frac{P_1 - P_s}{Q^a} \right)$$

is a function for determining the amount of gas being dissolved between $P_1$ and $P_s$; comparing the calculated volume-% gas to the target volume-% gas; and, if the calculated volume-% gas in the liquid carrier is greater or less than the target volume-% gas, lowering or raising the amount of gas in the liquid carrier.

In a method for controlling the output of processing a liquid-gas mixture in a batch mode, by: setting a quantitative target for volume-% of one or more gases in the mixture; subjecting the mixture to two different pressure states and measuring the apparent density of the mixture at each of the two pressure states; calculating the volume percentage of said gas in said liquid sample by using equation (28)

$$x\% = \frac{V_s}{V_s + V} \quad (28)$$

wherein $V_s$ is determined by equation (33)

$$V_s = \frac{T_s}{T} \frac{P_1 P_2}{P_s(P_2 - P_1)} \left(\frac{1}{\rho_1} - \frac{1}{\rho_2}\right) - \frac{RT_s}{C} \quad [33]$$

in which $P_1$ and $P_2$ are two different ambient pressures, $\rho_1$ and $\rho_2$ are apparent densities of the liquid sample measured at $P_1$ and $P_2$, respectively, $P_s$ and $T_s$ are standard pressure (1 atm) and temperature (0° C.), R is the constant of the Ideal Gas Law, T is the temperature of the liquid sample, and C is the gas solubility coefficient at a static state; and V is the volume of the gas-free liquid calculated through equation (32)

$$V = \frac{1}{\rho_1} - \left[\frac{P_2}{P_2 - P_1}\left(\frac{1}{\rho_1} - \frac{1}{\rho_2}\right) - \frac{RT}{C}\right] \quad [32]$$

in which T is the liquid temperature, and $P_1$, $P_2$, $\rho_1$, $\rho_2$, and R are the same as defined in this claim, comparing the calculated volume-% gas to the target volume-% gas; and, if the calculated volume-% gas in the liquid carrier is greater or less than the target volume-% gas, lowering or raising the amount of gas mixed in the liquid.

In a method for automatically controlling the output of a continuous process that requires mixing of a solid or liquid component with a liquid carrier component, by: setting a quantitative target for weight-% in a liquid carrier component of one or more solids—such as kaolin clay, calcium carbonate, titanium dioxide, or alumina trihydrate—to be coated onto a substrate such as a paper web, or setting a concentration of one or more liquids—such as a carbohydrate-containing liquid comprising corn syrup and high fructose corn syrup—to be blended with an aqueous liquid carrier component to make a syrup; continuously mixing said solids and/or liquids with the liquid carrier component; determining the true density, $\rho$, by employing equation (24)

$$\rho = \frac{1}{V} \quad (24)$$

wherein the volume, V, is calculated from equation (23)

$$V = \frac{1}{\rho_1} - \left[\frac{P_2}{P_2 - P_1}\left(\frac{1}{\rho_1} - \frac{1}{\rho_2}\right) - \frac{RT}{P_2 - P_1} g\left(\frac{\Delta P}{Q^a}\right)\right] \quad (23)$$

in which $P_1$ and $P_2$ are two different ambient pressures and $\Delta P = P_2 - P_1$, $\rho_1$ and $\rho_2$ are apparent densities of the liquid sample measured at $P_1$ and $P_2$, respectively, R is the constant of the Ideal Gas Law, T is the temperature of the liquid sample, Q is the flow rate, and $g(\Delta P/Q^a)$ is a function through which the gas solubility coefficients at a dynamic state are determined; calculating the weight-% of solids and/or the liquid concentration in the mixture from the true density $\rho$ so determined; comparing the calculated weight-% solids or concentration to the target weight-% solids or concentration; and, if the calculated weight-% solids or concentration is greater or less than the target weight-% solids or concentration, lowering or raising the amount of solids or liquids mixed in the mixing step.

In a method for controlling the output of a process with a liquid carrier that contains one or more gases, by: setting a quantitative target for volume-% of one or more gases in the liquid carrier component; calculating the volume percentage of said gas in said liquid sample by using equation (28)

$$x\% = \frac{V_s}{V_s + V} \quad (28)$$

wherein $V_S$ is determined by equation (37)

$$V_s = \frac{T_s}{T} \frac{P_1 P_2 \Delta V}{P_s(P_2 - P_1)} - \frac{RT_s}{C} \quad [37]$$

in which $T_s$ is 0° C., $P_1$ and $P_2$ are two different ambient pressures, $\Delta V$ is the volume difference of the free gas between $P_1$ and $P_2$, R is the constant of the Ideal Gas Law, T is the temperature of the liquid sample, $P_s$ is 1 atm, and C is the gas solubility coefficient at a static state; and V is the volume of the gas-free liquid in the sample chamber determined by equation (36)

$$V = V_{t1} - \left[\frac{P_2 \Delta V}{P_2 - P_1} - \frac{RT}{C}\right] \quad (36)$$

in which $V_{t1}$ is the volume of the gas-liquid mixture in the sample chamber at $P_1$, T is the ambient temperature, and $P_1$, $P_2$, $P_s$, $\Delta V$, R, and C are the same as being defined above; comparing the calculated volume-% gas to the target volume-% gas; and, if the calculated volume-% gas in the liquid carrier is greater or less than the target volume-% gas, lowering or raising the amount of gas in the liquid carrier.

In a method for controlling the output of a process for preparing a carbonated beverage, by: setting a quantitative target for a concentration of carbon dioxide to be blended into an aqueous medium; supplying carbon dioxide to the aqueous medium in a vessel and mixing those components to form a carbonated aqueous medium in the vessel at a preset "bottling" pressure $P_0$, wherein $P_0$ is the produced "bottling" pressure inside a sealed carbonated beverage container, at which pressure all of the free carbon dioxide is dissolved into the aqueous medium; diverting a carbonated aqueous medium sample from the vessel into a sample measurement chamber at the same "bottling" pressure $P_0$; reducing the aqueous medium pressure from $P_0$ to $P_1$ allowing the dissolved carbon dioxide to start to be released back to the aqueous medium in a free-bubble form while the volume of the sample measurement chamber to be expanded correspondingly; reducing the aqueous medium pressure further from $P_1$ to $P_2$ allowing more dissolved carbon dioxide to be released back to the aqueous medium in a free-bubble form while the volume of the measurement chamber to be expanded further; measuring the change in volume of the carbon dioxide liquid mixture between $P_1$ and $P_2$; determining the volume of free carbon dioxide, $V_s$, in the carbonated aqueous medium at the standard condition using equation (37)

$$V_s = \frac{T_s}{T} \frac{P_1 P_2}{P_s(P_2 - P_1)} \Delta V - \frac{RT_s}{C} \quad (37)$$

in which $P_1$ and $P_2$ are two different ambient pressures, $\Delta V$ is the change in sample volume between $P_1$ and $P_2$, $P_s$ and $T_s$ are standard pressure and temperature, T is the temperature of the liquid sample, C is the gas solubility coefficient at a static state, and R is the constant of the Ideal Gas Law; calculating the carbon dioxide concentration using equation (28)

$$x\% = \frac{V_s}{V_s + V} \qquad (28)$$

wherein $V_s$ is the volume of free carbon dioxide determined in step g.) and V is the volume of carbonated aqueous medium in the sample chamber at a preset "bottling" pressure $P_0$ upon which no free bubble should present; comparing the calculated carbon dioxide concentration to the target carbon dioxide concentration; and, if the calculated carbon dioxide concentration is greater or less than the target carbon dioxide concentration, lowering or raising the volume of carbon dioxide supplied.

The apparatus aspect of the present invention includes various embodiments, for instance:

A25—A dual core-module apparatus comprising: an apparatus having piping for processing 2- or 3-phase fluids at a dynamic state, said apparatus including two core-modules each comprising a density and temperature gauge having a pressure gauge located upstream thereof and a pressure gauge located downstream thereof, said two core-modules being operatively joined together by a pressure changing device;

A26—A single core-module apparatus comprising: an apparatus having piping for processing 2- or 3-phase fluids at either a dynamic or static state, said apparatus including a density and temperature gauge having a pressure gauge located upstream thereof and a pressure gauge located downstream thereof, said apparatus further including a pressure changing device being either a fluid control valve located either upstream of the pressure gauges or downstream of the pressure gauges or both or an optional pump;

A27—A static density measurement apparatus comprising: a process fluid reservoir and a pump operatively joined to piping through which a 2- or 3-phase fluid may be pumped, said apparatus including a density and temperature gauge having a pressure gauge located upstream or downstream thereof, said apparatus also including three fluid control valves located respectively downstream of the pressure gauge, upstream of the density gauge, and in a section of the piping that does not interconnect with either of said gauges, said apparatus further including a pressure regulator located upstream of all three fluid control valves; and A28—A static volume measurement apparatus comprising: a piston cylinder type of device having a sample measurement chamber with a precisely controllable/determinable volume for process 2- or 3-phase fluids, said device including a pressure and temperature gauge, said device also including a sensor for determining the volume of the said sample measurement chamber in terms of the cylinder displacement, said device further including inlet and outlet valves for handling said fluid in and out, respectively.

Moreover, additional apparatus embodiments are contemplated which would simplify those discussed above. One simplified example consists of the elimination of the pressure gauge either upstream or downstream of the density and temperature gauge. In this example, the remaining pressure gauge would be used to predict the pressure at the point of density measurement. Another example consists of incorporating pressure measurement into the combination density and temperature gauge. This new combination density, temperature and pressure gauge would eliminate the need for separate pressure gauge(s). Those skilled in the art can envision a number of continued apparatus simplifications, all of which would provide the required data, which consists of density, temperature and pressure at two pressure levels.

Finally, this invention contemplates various measurement procedures, including:

M29—A measurement procedure of obtaining data, on a continuous basis, for use in determining amounts of gas entrained or dissolved in a 2- or 3-phase fluid, which procedure comprises the steps of: providing an apparatus A25; processing the said fluid at a flow rate such that the pressure level differs between each of the dual core-modules by at least 1 psi or at least to the extent that two different apparent densities of said fluid differ from one another by at least 0.2%; collecting temperature, pressure and apparent density data from the first core-module while operating at steady-state conditions; collecting, SIMULTANEOUSLY, temperature, pressure and apparent density data from the second core-module while operating at steady-state conditions; and calculating entrained/dissolved gas using the algorithms (22)–(24) and (28) as described herein;

M30—A measurement procedure of obtaining data, at a dynamic state, for use in determining amounts of air entrained or dissolved in a 2- or 3-phase fluid, which procedure comprises the steps of: providing an apparatus A26; processing the said fluid through the core-module; collecting temperature, pressure and apparent density data at a first pressure level while operating at steady-state conditions; changing the pressure so that the pressure levels differ from one another by at least 1 psi or at least to the extent that two different apparent densities of said fluid differ from one another by at least 0.2% by either adjusting downstream/upstream pressure or increasing/reducing the flow rate; collecting temperature, pressure and apparent density data at a second pressure level while operating at steady-state conditions; and calculating entrained/dissolved gas using the algorithms (22)–(24) and (28) as described herein;

M31—A measurement procedure of obtaining data at a static state for use in determining amounts of air entrained or dissolved in a 2- or 3-phase fluid, which procedure comprises the steps of: providing an A25, A26, or A27 apparatus; subjecting/pressurizing the said fluid into the apparatus at a no-flow state; collecting temperature, pressure and apparent density data at a first pressure level when there is no longer any significant change in data; increasing or reducing the system pressure to levels that differ from one another by at least 1 psi or at least to the extent that two different apparent densities of said fluid differ from one another by at least 0.2%; collecting temperature, pressure and apparent density data at a second pressure level when there is no longer any significant change in data; and calculating entrained/dissolved gas using the algorithms (31), (32), (24), and (28) as described herein; and M32—A measurement procedure of obtaining data at a static state for use in determining amounts of air entrained or dissolved in a 2- or 3-phase fluid, which procedure comprises the steps of: providing an apparatus A28; diverting the said fluid into the sample measurement chamber; closing the sample chamber and pressurizing it to a first pressure level which could be below or above the atmospheric pressure depending on the degree of gas dissolved in the said fluid; collecting temperature, pressure and the volume of the sample chamber in terms of displacement at the first pressure level when there is no longer any significant change in data; compressing or expanding the volume of the sample chamber by increasing or reducing the pressure level so that the pressures differ from one another by at least 1 psi or at least to the extent that two different apparent densities of said fluid differ from one another by at least 0.2%; collecting temperature, pressure and the volume of the sample chamber in terms of displacement at a second pressure level when there is no longer any significant change in data; and calculating entrained/dissolved gas using the algorithms (35), (36), (24), and (28) as described herein.

BRIEF DESCRIPTION OF THE DRAWINGS

The present invention will be more fully understood from the detailed description given hereinbelow and from the accompanying drawings. These drawings are provided by way of illustration only, and thus do not in any way limit the present invention. In particular, it is noted that the hardware configurations depicted in these drawings are illustrative only (and not to scale). Those skilled in the art can easily develop alternative hardware configurations that will likewise obtain the benefits of the present invention.

DETAILED DESCRIPTION OF THE INVENTION

Figure 1:
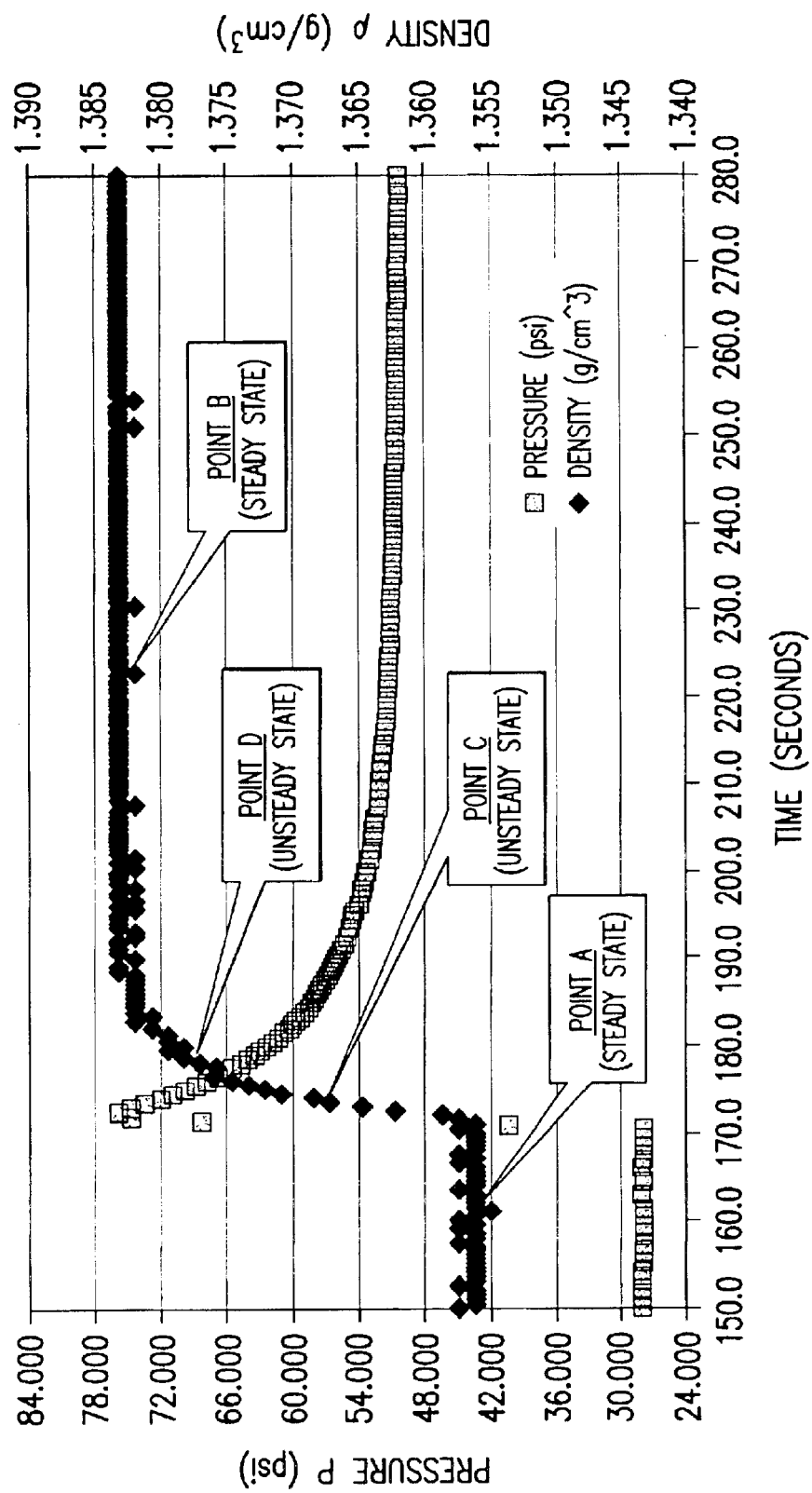
FIG. 1 shows the experimental curves of the density of a coating slurry, which contains entrained air, as a function of ambient pressure at steady and unsteady states.

The following symbols are used in connection with the description and claims pertaining to the present invention:

$P_1$, $P_2$: Ambient pressures at which the apparent densities of the liquid are measured. These pressures can be approximated by the average of the inlet and outlet pressures of a density meter P: Pressure of the gas being dissolved $V_1$, $V_2$: Volumes of the free gas entrained into a liquid at $P_1$ and $P_2$, respectively $n_1$, $n_2$: Moles of the free gas entrained into a liquid at $P_1$ and $P_2$, respectively $\rho_1$, $\rho_2$: Apparent densities of the liquid that contains entrained gas being measured at $P_1$ and $P_2$, respectively p: Gas-free true density of the liquid V: Gas-free volume of the liquid $V_{t1}$: Total volume of the liquid that contains entrained gas being measured at $P_1$ $\Delta V$: The volume difference of the free gas between $P_1$ and $P_2$ (a measurable value)

R: The constant of the Ideal Gas Law

T: Temperature of the process liquid/solution measured by a temperature sensor, assuming that the temperature is kept constant between the two measurement points ($T=T_1=T_2$)

Q: Flow rate $Q_1$, $Q_1$, ..., $Q_i$: Different flow rates for evaluating the influence of flow rate on gas solubility $\Delta P$: Pressure difference $\Delta P=P_2-P_1$ or $\Delta P=P_{II}-P_I$ $f(\Delta P, Q^a)$: A function of pressure difference and flow rate for determining the amount of dissolved gas at a dynamic state a: An index reflecting the weak influence of flow rate on gas solubility, which is generally less than 1, e.g., $a=\frac{1}{3}$ $g(\Delta P/Q_a)$: A function through which the gas solubility coefficients at a dynamic state can be determined $A_0, A_1, A_2, \ldots, A_i$: Gas solubility coefficients at a dynamic state C: Gas solubility coefficient at a static state $P_I$, $P_{II}$: Ambient pressures at which two apparent densities of the liquid are measured. They are used for the purpose of determining the gas solubility coefficients $V_I$, $V_{II}$: Volumes of the free gas entrained into a liquid at $P_I$ and $P_{II}$, respectively, which are used for the purpose of determining the gas solubility coefficient $n_I$, $n_{II}$: Moles of the free gas entrained into a liquid at $P_I$ and $P_{II}$, respectively, which are used for the purpose of determining the gas solubility coefficients $\rho_I$, $\rho_{II}$: Apparent densities of the liquid that contains entrained gas being measured at $P_I$ and $P_{II}$, respectively, which are used for determining the gas solubility coefficients $V_{II}|_{predicted}$: Predicted volume of free gas at $P_{II}$ based on Boyle's law $\rho_{predicted}$: Predicted gas-free liquid density based on Boyle's law $\rho^*$: Gas-free density of the liquid at a particular concentration, which is used explicitly in the process of determination of the gas solubility coefficients $P_g$: Gas pressure inside the entrained gas bubbles $\sigma$: Liquid surface tension r: The medium radius of the entrained gas bubbles $P_s$, $T_s$: Atmospheric pressure, $P_s=1$ atm (14.7 psi) and standard temperature, $T_s$ 0° C.

$n_s$, $V_s$: Moles and volume of free gas at $P_s$ and $T_s$ y %: Volume percentage of free gas being dissolved/exsolved between Points I and II x %: Volume percentage of free gas at $P_s$ and $T_s$ $$S_i = \frac{1}{RT}\left[P_I\left(\frac{1}{\rho_I} - \frac{1}{\rho^*}\right) - P_{II}\left(\frac{1}{\rho_{II}} - \frac{1}{\rho^*}\right)\right]\bigg|_{Q=Q_i}$$

is an intermediate variable used when solving a group of linear equations for the gas solubility coefficients.

In this invention, it is assumed that the average size of the entrained gas bubbles is sufficiently large, e.g., $r \geq 1$ mm (0.079°). This would allow that the ambient pressure, P, which substitutes the gas pressure, $P_g$, inside the gas bubbles, could conveniently be used while still maintain a sufficient accuracy.

As such, the ambient pressure can consequently be substituted into the ideal gas law PV=nRT, giving the volumes of free gas in a liquid at different pressures $$V_1 = \frac{n_1 RT}{P_1} \quad (6)$$

$$V_2 = \frac{n_2 RT}{P_2} \quad (7)$$

NOTE: assuming $T=T_1=T_2$.

The volume difference, $\Delta V$ between $P_1$–$P_2$ is the reflection of the change in volume of the entrained gas only, since the liquid itself is incompressible. Equation (6) and (7) can therefore be combined to $$V_1 - V_2 = \Delta V = \left(\frac{n_1}{P_1} - \frac{n_2}{P_2}\right)RT. \quad (8)$$

$\Delta V$, in general, can be determined either DIRECTLY by measuring the changes in volume, herein referred to as DIRECT MEASUREMENT; or INDIRECTLY by measuring the changes in apparent density, herein referred to as INDIRECT MEASUREMENT. By assuming that the unit of mass equals 1, the relationship between these two measurements can readily be found as $$\Delta V = \frac{1}{\rho_1} - \frac{1}{\rho_2}. \quad (9)$$

Equation (8) can be rewritten as $$P_2 n_1 - P_1 n_2 = \frac{P_1 P_2}{RT}\left(\frac{1}{\rho_1} - \frac{1}{\rho_2}\right). \quad (10)$$

Earlier experiments had demonstrated, as the examples shown in FIG. 1, that change of ambient pressure would cause change of liquid density as a result of free gas dissolving into or exsolving from the liquid. At an equilibrium state, where the process of gas dissolving/exsolving is COMPLETE between two equilibrium state points, for example Point A and B in FIG. 1, the amount of dissolved/exsolved gas would be maximized. In contrast, at a non-equilibrium or dynamic state, where the process of gas dissolving/exsolving is INCOMPLETE, e.g., between Point C and D in FIG. 1, only a portion of, otherwise, the totally dissolvable gas will be dissolved into or exsolved from the liquid. The dissolved/exsolved portion of gas at such a state, for example between two non-equilibrium state points, C and D, is a function of not only the pressure difference, $P_D$–$P_C$, but also the time elapsed between Point C and D.

The amount of dissolved/exsolved gas between two different pressure points is, as matter of fact, determinable. Provided the gas-free liquid density, $\rho^*$ is known, which can precisely be obtainable by using, for example, a DMA 4500 density meter, the actual volume of free gas at $P_I$ and $P_{II}$ can be determined as $$V_I = \frac{1}{\rho_I} - \frac{1}{\rho^*} \text{ and } V_{II} = \frac{1}{\rho_{II}} - \frac{1}{\rho^*} \quad (11)$$

respectively. While according to Boyle's law, which assumes no gas being dissovled/exsolved between Points I and II, the predicted volume of free gas at $P_{II}$ would be $$V_{II}|_{predicted} = \frac{P_I V_I}{P_{II}} \quad (12)$$

The volume percentage of free gas, y %, being dissolved/exsolved between points I and II can therefore be attained as $$y\% = \frac{V_{II}|_{predicted} - V_{II}}{V_{II}|_{predicted}}. \quad (13)$$

The experimental results listed in Table 1 & Table 2 demonstrate how the percentage of free gas being dissolved/exsolved might change under the influence of pressure differences and time elapsed between Points I and II.

TABLE 1

% dissolved/exsolved air of one polyvinyl alcohol solution (7.00% PVA T340) at different test conditions

| Time Elapsed t between Point I & II (sec) | Pressure Difference ΔP between Point I & II (atm) | Predicted % Free-Air$_{state\ II}$ (Boyle's law) | Actual % Free-Air$_{state\ II}$ | % Free-Air Dissolved between Point I & II |
|---|---|---|---|---|
| 12 | 5.69 | 11.6% | 7.0% | 39.7% |
| 14 | 4.18 | 12.5% | 7.8% | 37.6% |
| 24 | 1.98 | 13.2% | 10.3% | 22.0% |
| 106 | 0.42 | 13.8% | 13.2% | 4.3% |

TABLE 2

% dissolved/exsolved air of another polyvinyl alcohol solution (9.16% PVA 325) at different test conditions

| Time Elapsed t between Point I & II (sec) | Pressure Difference ΔP between Point I & II (atm) | Predicted % Free-Air$_{state\ II}$ (Boyle's law) | Actual % Free-Air$_{state\ II}$ | % Free-Air Dissolved between Point I & II |
|---|---|---|---|---|
| 12 | 3.93 | 5.8% | 3.1% | 47.8% |
| 20 | 1.57 | 5.4% | 3.2% | 40.1% |
| 32 | 0.69 | 5.1% | 4.0% | 22.1% |
| 36 | 0.56 | 4.8% | 3.9% | 18.6% |

The experimental results confirmed that using the approach of Boyle's law tends to overestimate the amount of entrained free-gas, which, in turn, leads to an overestimation of the gas-free, true liquid density. In general, increasing the level of air entrainment tends to increase the amount of overestimation, in terms of $\rho_{predicted}-\rho^*$. It was found that $\rho_{predicted}-\rho^*$ was also primarily depended on the pressure difference between the two measuring points since the change of $\Delta P$ changes the amount of free gas being dissolved/exsolved as illustrated in the above tables.

U.S. Pat. No. 6,496,781 illustrates the prediction of % solids as a function of the measured liquid density. As $\rho_{predicted}-\rho^*$ increases to exceed a certain amount, for example, $\rho_{predicted} - \rho^* = 1.0297 - 1.0182 > 0.01$ g/cm³ when $\Delta P = 4.18$ atm and % entrained free-air=7.8%, it may give a significant impact on the precision of % solids prediction as depicted in Table 3.

TABLE 3

The impact of changing $\rho_{predicted} - \rho^*$, due to change of % entrained air and $\Delta P$ when using Boyle's law model, on the precision of % solids prediction (assuming dried solid density = 2.000 g/cm³ and air-free, true liquid density = 1.2000 g/cm³)

| $\rho_{predicted} - \rho^*$ (g/cm³) | Predicted % Solids | Actual % Solids | Overestimated % Solids |
|---|---|---|---|
| 0.004 | 33.8% | 33.3% | 0.5% |
| 0.010 | 34.6% | 33.3% | 1.3% |
| 0.020 | 36.0% | 33.3% | 2.7% |
| 0.040 | 38.6% | 33.3% | 5.3% |

To ensure a higher precision on entrained gas calculation at a dynamic state, the amount of dissolved/exsolved gas, nevertheless, must be taken into consideration as well. New formulas would therefore be needed for the real process of a 2 or 3-phase fluid flow, in which the fluid flows from a high-pressure Point II to a low-pressure Point I, accompanied by a portion of the dissolved gas being exsolved in the form of free-gas bubbles at the low-pressure point. In such a dynamic state, the amount of exsolved gas between the two unsteady-state measurement points would primarily depend upon a dominating factor: the pressure difference, $P_{II} - P_I$, and, also, the time elapsed for a fluid particle flowing from Point II to Point I. The latter, in turn, can also be expressed in terms of flow rate, Q, since the distance between II and I for any certain flow loop is a constant. This gives $$n_u - n_u = f((P_{II} - P_I), Q) \quad (14).$$

In general, it can be anticipated, as observed in practice, that the amount of dissolved/exsolved gas between Point I and II increases as the pressure difference increases, and decreases as the flow rate increases.

Table 1 and 2 indicate that $n_I - n_{II}$, is strongly proportional to $P_{II} - P_I$ while may be inversely correlated with Q in a weak manner. The equation (14) can then be expressed as $$n_I - n_{II} = g\left(\frac{\Delta P}{Q^a}\right) \quad (15)$$

where a is an index less than 1, e.g., a ⅓, and $g(\Delta P/Q^a)$ is a function of $\Delta P$ and Q to be determined. Using the result of (10), (15) can be rewritten as $$n_I = \frac{1}{RT} \frac{P_I P_{II}}{\Delta P}\left(\frac{1}{\rho_I} - \frac{1}{\rho_{II}}\right) - \frac{P_I}{\Delta P} g\left(\frac{\Delta P}{Q^a}\right). \quad (16)$$

By measuring the gas-free liquid density, $\rho^*$, the volumes of free gas, $V_1$, at $P_1$ can be determined as defined in (11), which in combination with the outcome of (6) leads to $$n_I = \frac{P_I}{RT}\left(\frac{1}{\rho_I} - \frac{1}{\rho^*}\right). \quad (17)$$

By solving (16) and (17) simultaneously, it becomes $$g\left(\frac{\Delta P}{Q^a}\right) = \frac{1}{RT}\left[P_I\left(\frac{1}{\rho_I} - \frac{1}{\rho^*}\right) - P_{II}\left(\frac{1}{\rho_{II}} - \frac{1}{\rho^*}\right)\right]. \quad (18)$$

Figure 2:
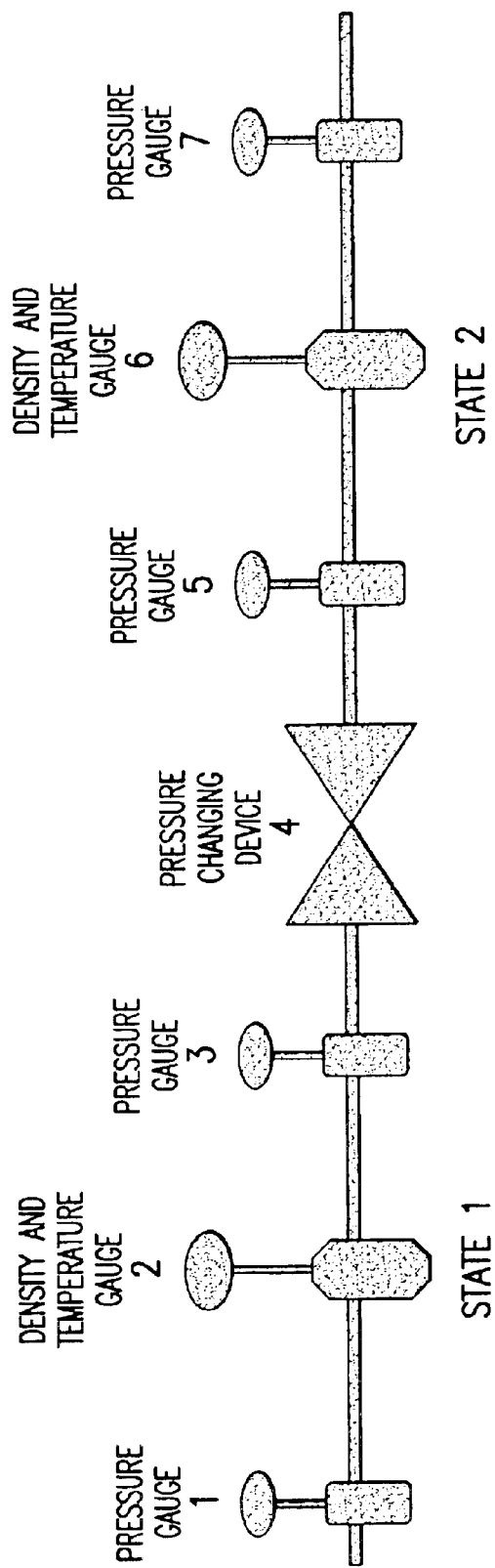
FIG. 2 is a schematic representation of an indirect measurement apparatus embodiment of the present invention. This embodiment continuously measures state conditions of pressure difference, temperature, and density at two different pressure states.

The function $g(\Delta P/Q^a)$ can explicitly be solved at this point when a certain type of function, e.g., a polynomial function, $$g\left(\frac{\Delta P}{Q^a}\right) = A_0 + A_1\left(\frac{\Delta P}{Q^a}\right) + A_2\left(\frac{\Delta P}{Q^a}\right)^2 + \ldots + A_i\left(\frac{\Delta P}{Q^a}\right)^i,$$

is chosen. Running the indirect measurement apparatus as illustrated in FIG. 2 at different flow rates, $Q_1, Q_2, \ldots, Q_i$, for example, the gas solubility coefficients, $A_0, A_1, \ldots, A_i$, can become available by solving a set of linear equations (19)

$$A_0 + A_1\left(\frac{\Delta P}{Q^a}\right) + A_2\left(\frac{\Delta P}{Q^a}\right)^2 + \ldots + A_i\left(\frac{\Delta P}{Q^a}\right)^i = S_1\bigg|_{Q=Q_1} \quad (19)$$

$$A_0 + A_1\left(\frac{\Delta P}{Q^a}\right) + A_2\left(\frac{\Delta P}{Q^a}\right)^2 + \ldots + A_i\left(\frac{\Delta P}{Q^a}\right)^i = S_2\bigg|_{Q=Q_2}$$

$$\ldots$$

$$A_0 + A_1\left(\frac{\Delta P}{Q^a}\right) + A_2\left(\frac{\Delta P}{Q^a}\right)^2 + \ldots + A_i\left(\frac{\Delta P}{Q^a}\right)^i = S_i\bigg|_{Q=Q_i}$$

where $$S_1 = \frac{1}{RT}\left[P_I\left(\frac{1}{\rho_I} - \frac{1}{\rho^*}\right) - P_{II}\left(\frac{1}{\rho_{II}} - \frac{1}{\rho^*}\right)\right]\bigg|_{Q=Q_1} \quad (20)$$

$$S_2 = \frac{1}{RT}\left[P_I\left(\frac{1}{\rho_I} - \frac{1}{\rho^*}\right) - P_{II}\left(\frac{1}{\rho_{II}} - \frac{1}{\rho^*}\right)\right]\bigg|_{Q=Q_2}$$

$$\ldots$$

$$S_i = \frac{1}{RT}\left[P_I\left(\frac{1}{\rho_I} - \frac{1}{\rho^*}\right) - P_{II}\left(\frac{1}{\rho_{II}} - \frac{1}{\rho^*}\right)\right]\bigg|_{Q=Q_i}.$$

Likewise, the theory of multiple linear regression could also be utilized here for an estimation on the gas solubility coefficients. Once the gas solubility coefficients are determined through a one-time measurement, they would also be applicable for a group of solutions, with similar constituents, running at different operation conditions, e.g., different flow rates, different % solids, different % entrained gas, and so on.

In practice, the true densities of the majority of industrial liquids are measurable. Their gas solubility coefficients at a dynamic state can readily be determined through the approach as illustrated above. For the liquid densities which are not directly measurable due to some particular constraints, e.g. the existence of extremely stable gas bubbles in high % solids, high viscous coating slurries, several alternate methods might be adopted to obtain a reasonable estimation of the related gas solubility coefficients. Some of the options are: diluting the high % solids down to a level in which the entrained gas bubbles would be no longer stable, increasing the liquid ambient pressure up to a level at which most of the free gas bubbles would be dissolved, using the known gas solubility coefficients for the solutions with the similar constituents, and so on.

With the availability of the gas solubility coefficients and therefore $g(\Delta P/Q^a)$, the moles of free gas, $n_1$, when the system is operating between two different pressures, $P_1$ and $P_2$, can be found as $$n_1 = \frac{1}{RT}\frac{P_1 P_2}{P_2 - P_1}\left(\frac{1}{\rho_1} - \frac{1}{\rho_2}\right) - \frac{P_1}{P_2 - P_1} g\left(\frac{\Delta P}{Q^a}\right). \quad [21]$$

This makes the volume of free air, $V_1$, at $P_1$ to be attainable $$V_1 = \frac{P_2}{P_2 - P_1}\left(\frac{1}{\rho_1} - \frac{1}{\rho_2}\right) - \frac{RT}{P_2 - P_1} g\left(\frac{\Delta P}{Q^a}\right) \quad [22]$$

and the air-free volume of the liquid, V, to be $$V = V_{tl} - V_1 = \frac{1}{\rho_1} - \left[\frac{P_2}{P_2 - P_1}\left(\frac{1}{\rho_1} - \frac{1}{\rho_2}\right) - \frac{RT}{P_2 - P_1} g\left(\frac{\Delta P}{Q^a}\right)\right]. \quad [23]$$

The gas-free, true density can also be obtained as $$\rho = \frac{1}{V} \quad [24]$$

To determine the moles of free air, $n_s$, at the atmospheric pressure, $P_s$, the difference of dissolved air, $\Delta n_s$, between $P_1$ and $P_s$ should first be calculated using (15)

$$\Delta n_s = g\left(\frac{P_1 - P_2}{Q^a}\right). \quad [25]$$

The moles of free gas entrained into the liquid n, can then be expressed as $$n_s = \quad [26]$$

$$n_1 + \Delta n_s = \frac{1}{RT}\frac{P_1 P_2}{P_2 - P_1}\left(\frac{1}{\rho_1} - \frac{1}{\rho_2}\right) - \frac{P_1}{P_2 - P_1} g\left(\frac{\Delta P}{Q^a}\right) + g\left(\frac{P_1 - P_s}{Q^a}\right).$$

The volume of free air, $V_s$, at the atmospheric pressure, $P_s$, is therefore $$V_s = \frac{n_s RT_s}{P_s} = \quad [27]$$

$$\frac{T_s}{T}\frac{P_1 P_2}{P_s(P_2 - P_1)}\left(\frac{1}{\rho_1} - \frac{1}{\rho_2}\right) - \frac{RT_s}{P_s}\left(\frac{P_1}{P_2 - P_1} g\left(\frac{\Delta P}{Q^a}\right) - g\left(\frac{P_1 - P_s}{Q^a}\right)\right).$$

The volume percentage of free air, $x\%$, at $P_s$ and $T_s$ can consequently be attained as $$x\% = \frac{V_s}{V_s + V}. \quad [28]$$

When the time elapsed between two measuring points becomes extremely short, which could possibly achieved with either a extremely high flow rate, e.g., $Q\to\infty$, or a very short distance between the two measuring points, the right side of equation (15) approaches zero, thus $$n_1 - n_2 = \Delta n = g\left(\frac{\Delta P}{Q^a}\right) \to 0,$$

yielding $n_1 \approx n_2 = n$. This would result in an approximation to be identical to Boyle's law.

At a static state, the amount of gas being dissolved/exsolved can directly be attained from Henry's law, given as $$n_I - n_{II} = \frac{1}{C}(P_{II} - P_I) \quad [29]$$

where C is the gas solubility coefficient at a static state. The gas solubility coefficient, C, under the circumstance of the indirect measurement, can readily be determinable through a one-time measurement of the gas free liquid density, $\rho^*$ $$C = RT(P_{II} - P_I)\left[P_I\left(\frac{1}{\rho_I} - \frac{1}{\rho^*}\right) - P_{II}\left(\frac{1}{\rho_{II}} - \frac{1}{\rho^*}\right)\right]^{-1}. \quad [30]$$

For the indirect measurement, the determination of C yields the parameters of interest, the volume of free air, $V_1$, at pressure $P_1$ to be $$V_1 = \frac{P_2}{P_2 - P_1}\left(\frac{1}{\rho_1} - \frac{1}{\rho_2}\right) - \frac{RT}{C} \quad [31]$$

and the air-free volume of the liquid, V, to be $$V = \frac{1}{\rho_1} - \left[\frac{P_2}{P_2 - P_1}\left(\frac{1}{\rho_1} - \frac{1}{\rho_2}\right) - \frac{RT}{C}\right] \quad [32]$$

and the volume of free air, $V_s$, at the standard conditions to be $$V_s = \frac{T_s}{T}\frac{P_1 P_2}{P_s(P_2 - P_1)}\left(\frac{1}{\rho_1} - \frac{1}{\rho_2}\right) - \frac{RT_s}{C}. \quad [33]$$

The gas-free, true density, $\rho$, and volume percentage of free air, $x\%$, can be obtained in the same manner as defined in (24) and (28), respectively.

When the volume of gas-free liquid is measurable through one time measurement, which can be achieved, for example, by pressurizing the system high enough to dissolve all of the free gas, the volumes of the free gas, $V_I$ and $V_{II}$, at $P_I$ and $P_{II}$, respectively, are directly computable. The gas solubility coefficient, C, under the circumstance of the direct measurement, can therefore be found as $$C = \frac{RT(P_{II} - P_I)}{P_I V_I - P_{II} V_{II}}. \quad [34]$$

For the direct measurement, the determination of C leads the parameters of interest, the volume of free air, $V_1$, at pressure $P_I$ to be $$V_1 = \frac{P_2 \Delta V}{P_2 - P_1} - \frac{RT}{C} \quad [35]$$

and the air-free volume of the liquid, V, to be $$V = V_{tl} - \left[\frac{P_2 \Delta V}{P_2 - P_1} - \frac{RT}{C}\right] \quad [36]$$

and the volume of free air, $V_s$, at the standard conditions to be $$V_s = \frac{T_s}{T} \frac{P_1 P_2 \Delta V}{P_s(P_2 - P_1)} - \frac{RT_s}{C}. \qquad [37]$$

The gas-free, true density, ρ, and volume percentage of free air, x %, can be obtained in the same fashion as given in (24) and (28), respectively.

INDUSTRIAL APPLICABILITY

While the focus of the discussion in this application is often on "air", this invention can also be applied to the determination of amounts of any gas that is entrained and/or dissolved in any liquid. For instance, one important application of this invention is in the manufacture and processing of carbonated beverages, in which much more carbon dioxide gas than air is entrained and dissolved in the liquid carrier. Likewise, the present invention can be applied to processes conducted under an inert atmosphere, in which the gas may be nitrogen, helium, or another "inert" gas instead of (or in addition to) air.

U.S. Pat. No. 6,496,781 B1, entitled IMPROVED MIXTURE CONCENTRATION CONTROL IN MANUFACTURING PROCESSES, issued on Dec. 17, 2002. Some (but by no means all) embodiments of the present invention can be used to make certain control methods described in that patent even more accurate. Accordingly, the entire disclosure of that patent is hereby expressly incorporated by reference. Also, the present inventors are filing concurrently herewith an application Ser. No. 10/644,994 entitled APPARATUS AND METHOD FOR REAL TIME DETERMINATION OF DENSITY AND RELATED PARAMETERS IN MANUFACTURING PROCESSES. That application, which is identified as assumes no gas solubility in order to simplify implementation of its invention. The entire disclosure of that application is hereby expressly incorporated by reference.

EXAMPLES

Example 1

Figure 6:
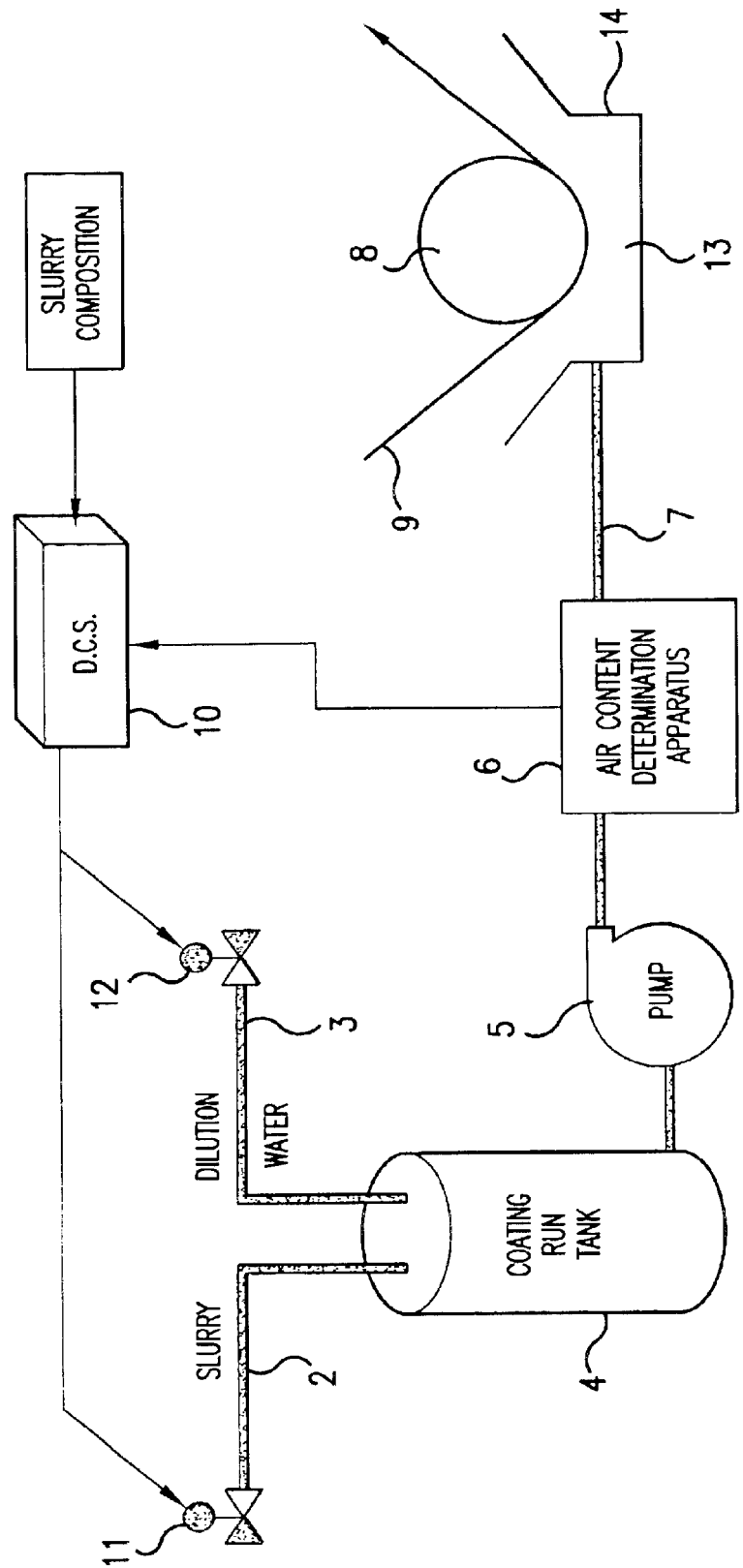
FIG. 6 is a schematic representation of an industrial coating line having an on-line measurement system in accordance with the present invention integrated into it.
Figure 7:
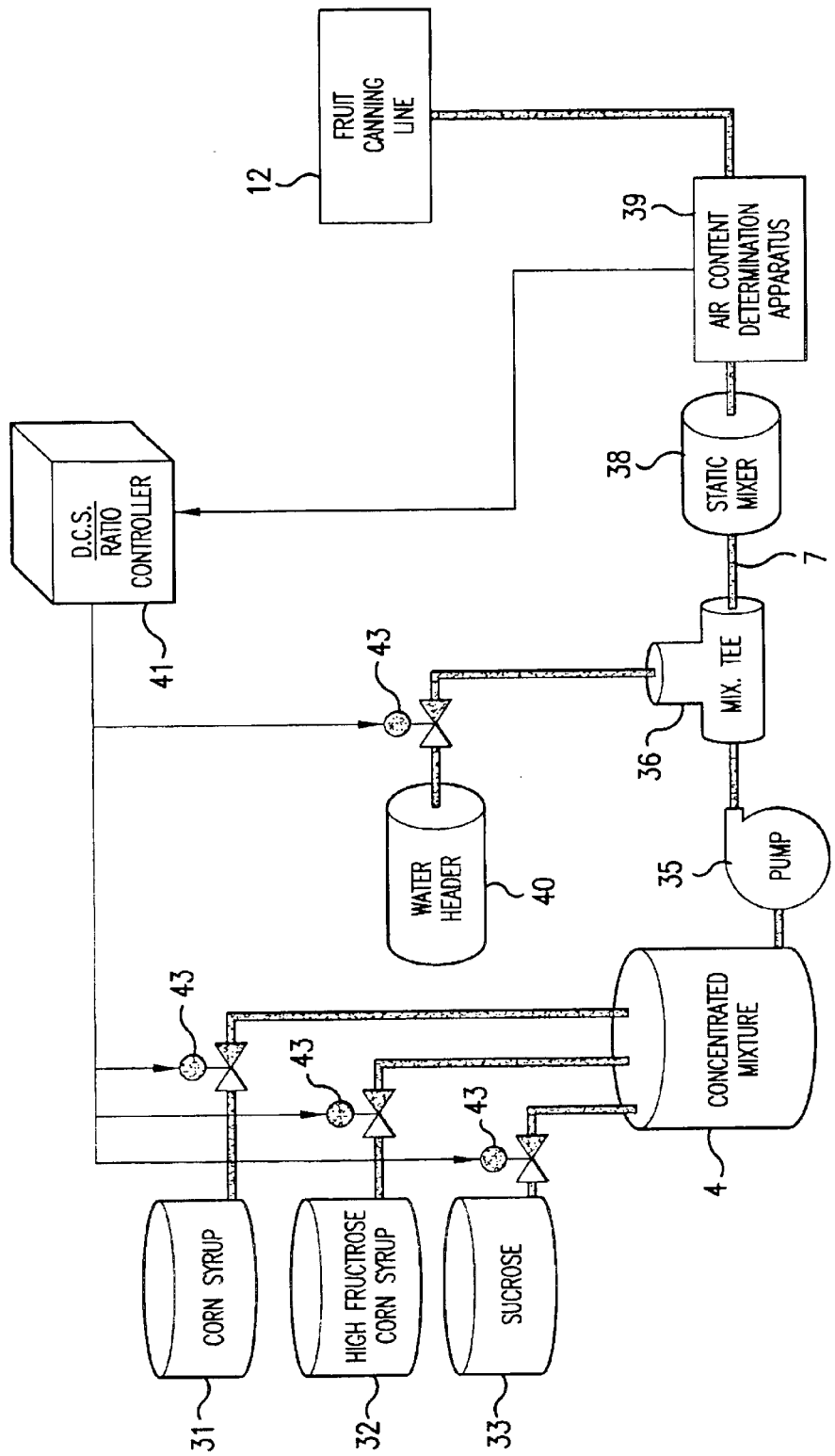
FIG. 7 is a schematic representation of a fruit canning line having a Distributed Control System operating in accordance with this invention.
Figure 8:
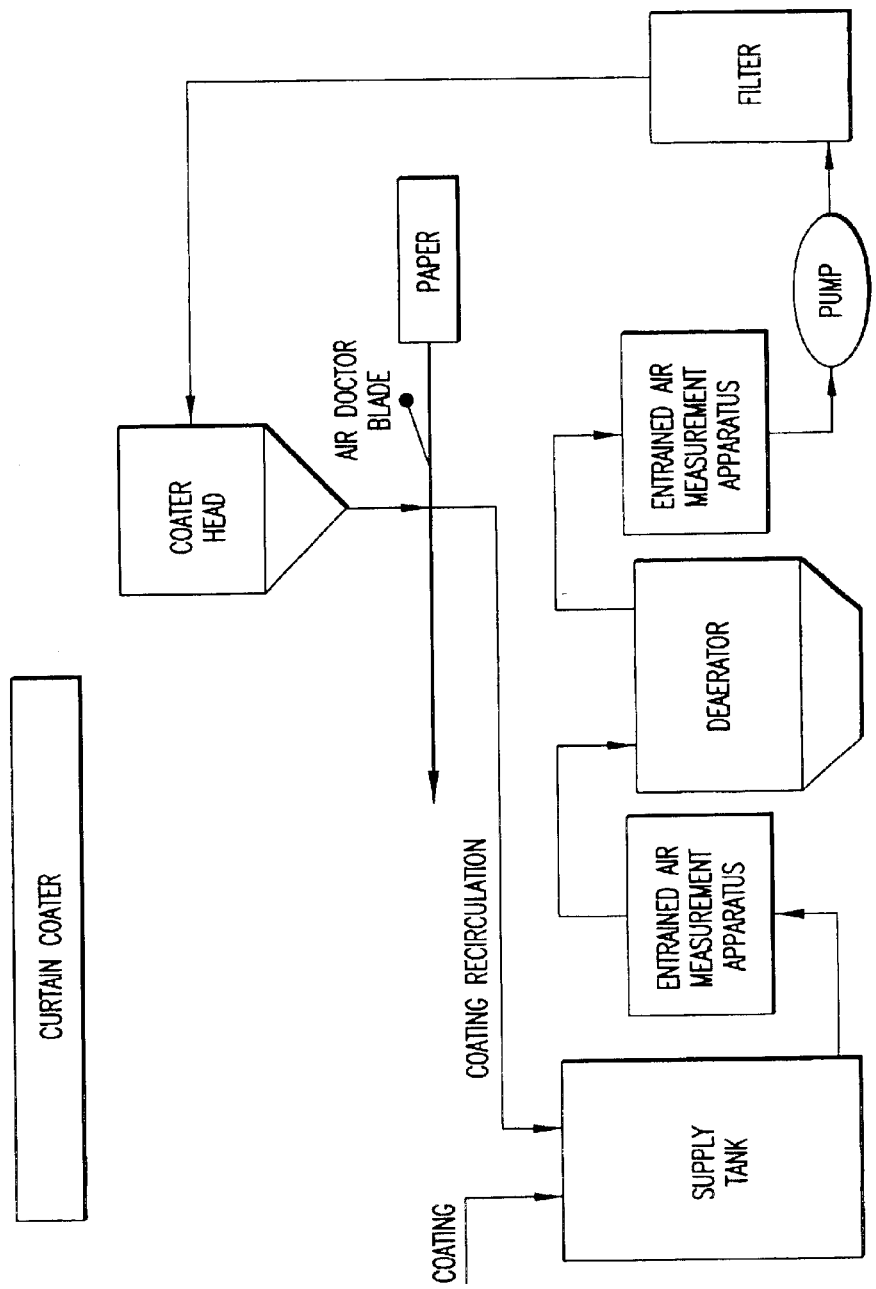
FIG. 8 is a schematic representation of a coating system including two applications of this invention installed directly in the process flow line.

Dual Core-Module Apparatus for the Measurement of Entrained and Dissolved Air Content and True Liquid Density in Liquids on a Continuous Basis FIG. 2 depicts one particular hardware configuration used to dynamically measure state conditions that can be employed to practice the invention disclosed herein. This embodiment requires the measurement of fluid density and temperature at each of two pressure states, as well as measurement of the pressure at which the density was measured. The embodiment of FIG. 2 can be positioned, for example, within a process flow line of a manufacturing process, as shown in FIGS. 6, 7, and 8. In another application, this apparatus could be positioned in a piping sample line that runs parallel to the manufacturing process flow line, such as in FIG. 9.

In the embodiment depicted in FIG. 2, the density and temperature at the first pressure state (STATE 1) are measured with instrumentation familiar to those skilled in the art, such as a combination density, temperature, and mass flow meter, density and temperature gauge 2, operating on the principles of coriolis technology. To determine the pressure at which this density is measured, a variety of techniques can be applied. In this embodiment, the system pressure is measured using pressure gauges 1 and 3 both before and after the density and temperature gauge 2. In this application, the average pressure across 2 is used as the desired pressure measurement. However, the method for determining the required pressure measurement would be based on the design of device 2. This value could be obtained through modeling techniques, or, with an advanced combination version of instrument 2 that includes a pressure measurement.

The process fluid then passes through an optional pressure changing device 4 such as a partially closed valve or an orifice. This device is not always necessary since the process fluid may experience a sufficient loss of pressure due to normal pressure drop related to fluid transport through a piping system. Sufficient pressure drop is defined as that which allows for a measurable change in density of the air-fluid mixture being measured. The fluid then passes through a series of instruments 5, 6, and 7 that perform in the same fashion as described above for instruments 1, 2, and 3.

These two sets of pressure, temperature, and density data may then be used in the processes of the algorithms (22)–(24) and (28) for entrained/dissolved air calculation, which are described in detail hereinabove.

This hardware configuration allows a no-time delay, instantaneous determination on the parameters of interest at a dynamic state. If needed, such a configuration is also capable of operating at a static state by employing the algorithms (31), (32), (24), (28). Since the measurement is made in terms of the change in apparent density, the uniformity of a gas-liquid mixture is critical to the accuracy with this configuration. The cost of this hardware configuration is comparatively high due to its dual core-modules, i.e., one coriolis meter and two pressure sensors for each of the two modules.

Example 2

Figure 3:
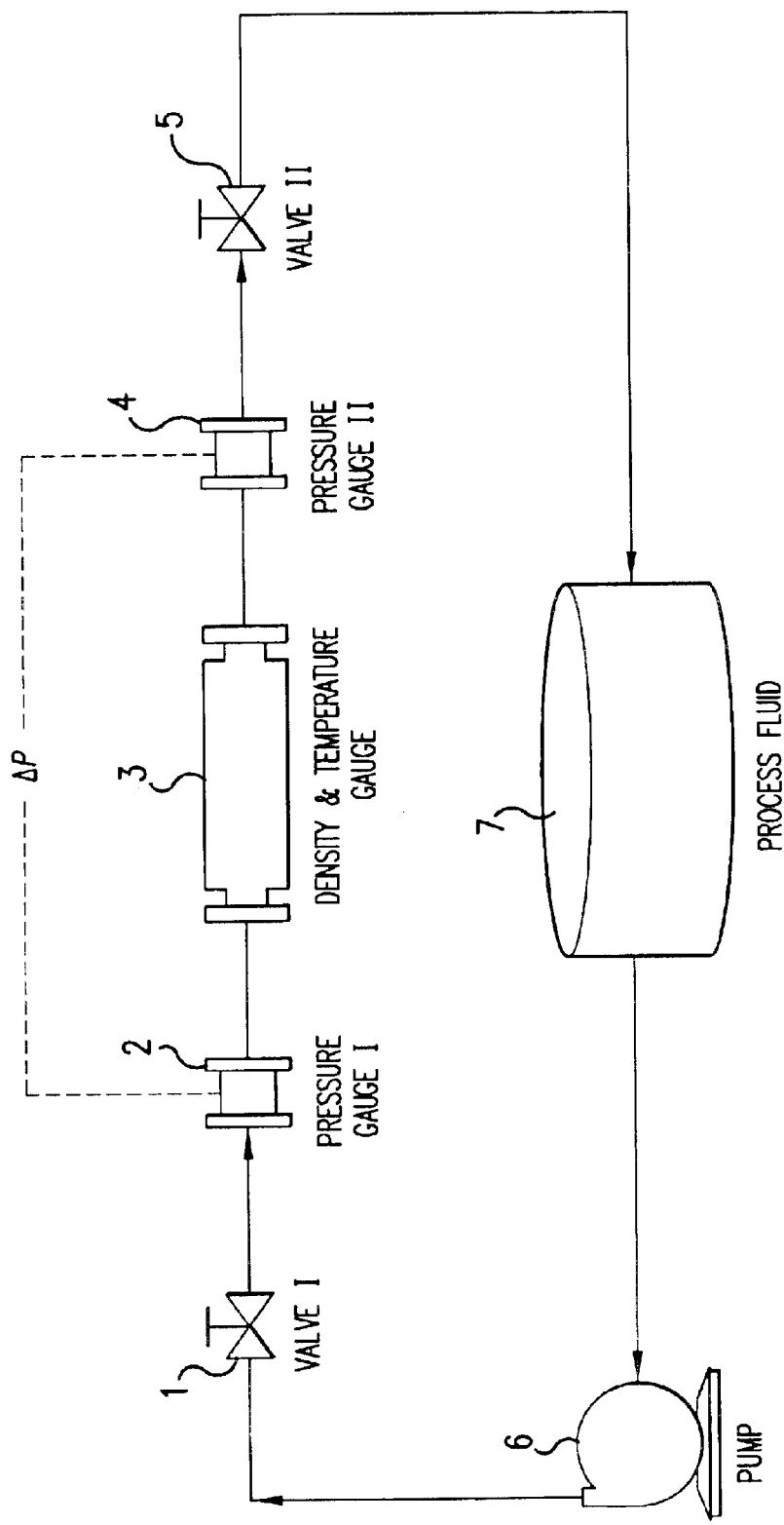
FIG. 3 is a schematic representation of another indirect measurement apparatus embodiment of the present invention. This embodiment dynamically measures density, pressure difference, and temperature at two different levels of pressures, which can be manipulated either by altering the flow rate with an optional pump or by changing the up/downstream pressures with the valves opened correspondingly.
Figure 9:
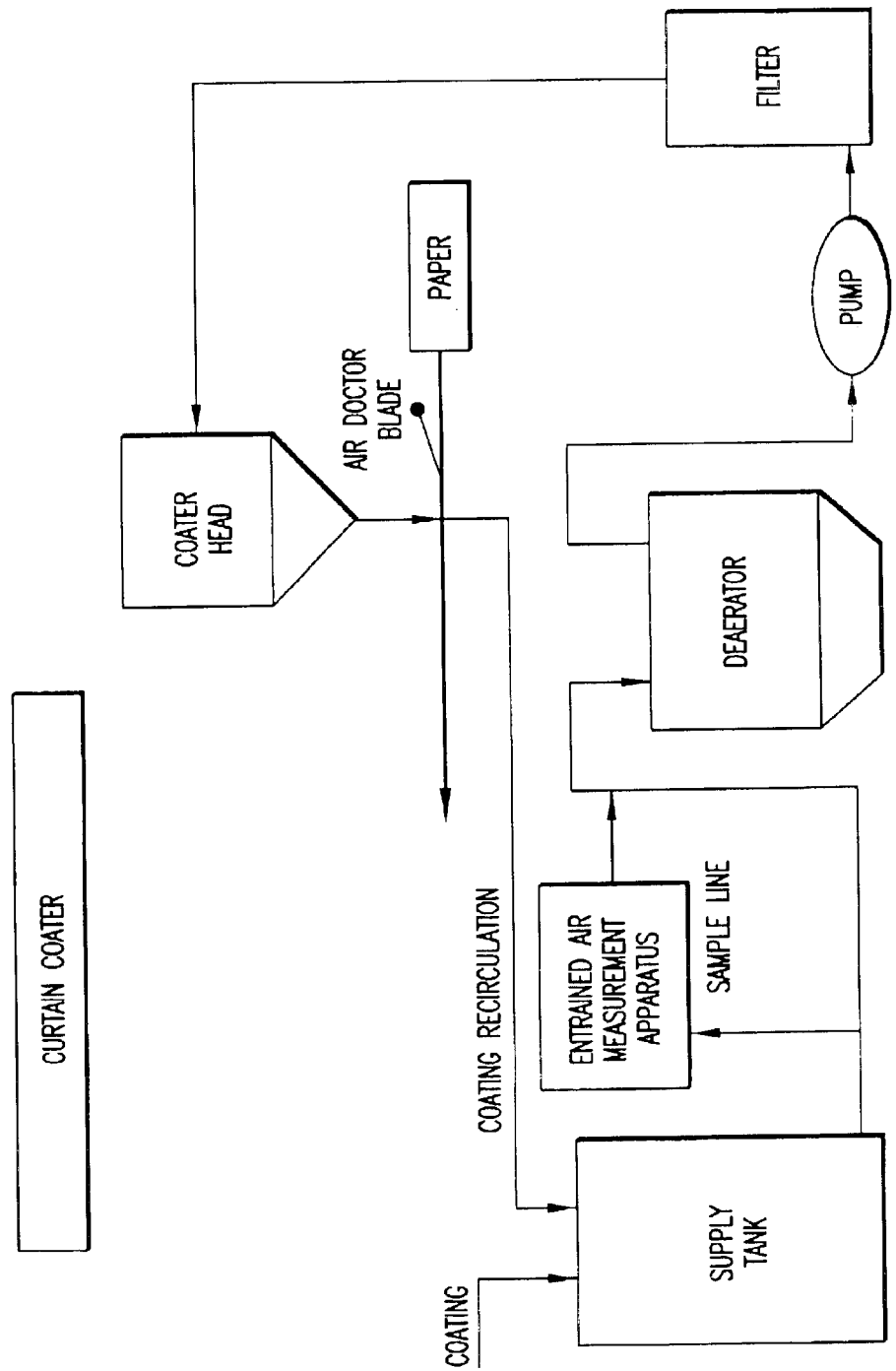
FIG. 9 is a schematic representation of a coating system including an application of this invention installed in a sample line.

Single Core-Module Apparatus for the Measurement of Entrained and Dissolved Air Content and True Liquid Density in Liquids at a Dynamic State FIG. 3 is a schematic of another particular hardware configuration used to dynamically measure the state conditions needed to practice the invention disclosed herein. The required parameters of measurement are fluid density and temperature at two different levels of pressure, as well as the pressure upon which the density values are determined. The embodiment of FIG. 3 can be positioned similarly to that illustrated in the previous example, within a process flow line of a manufacturing process, as shown in FIGS. 6, 7, and 8, or parallel to the manufacturing process flow line, as depicted in FIG. 9.

The output of density and temperature in this embodiment, as in Example 1, is provided by density and temperature gauge 3. This device can be an instrument familiar to those skilled in the art, such as a coriolis meter. The pressure upon which the density value is determined can be measured with different types of techniques. In this application, the required pressure can be estimated, as depicted in Example 1, based on the average of the pressure measurements from pressure gauges 2 and 4, which are positioned before and after device 3, respectively. To minimize the interference on regular flow streamlines, which might cause additional unwanted pressure changes, the sensors of pressure gauges 2 and 4 can, for instance, be mounted flush with the inner surface of the pipe. The determination of the required pressure can also be coupled with the design of density and pressure gauge 3 itself. This can be achieved, for example, by a more sophisticated instrument 3 that incorporates a couple of internally mounted pressure sensors.

The first set of density, pressure, and temperature data can dynamically be measured at a relatively low pressure. The second set data can then dynamically be measured, right after the first measurement, at a relatively high pressure. Such an order of measurement can be accomplished, for example, by reducing the flow rate with an optional pump or by increasing upstream pressure with the valves opened widely. The order of measurements can also be reversed with the respective devices set accordingly. Depending on the desired flexibility, functionality, and equipment cost, a real measurement system can comprise of either devices 1, 2, 3, 4 or devices 1, 2, 3, 4, 5 or devices 2, 3, 4, 6 or any other combination of those as required by this embodiment. These two sets of data can then be put into execution of the algorithms (22)–(24) and (28) for both entrained and dissolved air calculation.

This hardware configuration allows a dynamic determination on the parameters of interest, with a cycle time that is required for setting the coriolis meter being operated at two different pressures. Since no equilibrium is needed, its required cycle time, in general, can be much shorter than the normal cycle time, which is reported to be 3–5 minutes, with the prior arts. If needed, such a configuration is also capable of operating at a static state by applying the algorithms (31), (32), (24), (28). Because of the indirect measurement, the measurement accuracy with this configuration might be affected by the uniformity of a gas-liquid mixture. The cost of this hardware configuration is comparatively low since only a single core-module is required, i.e., one coriolis meter and two pressure sensors.

Example 3

Figure 4:
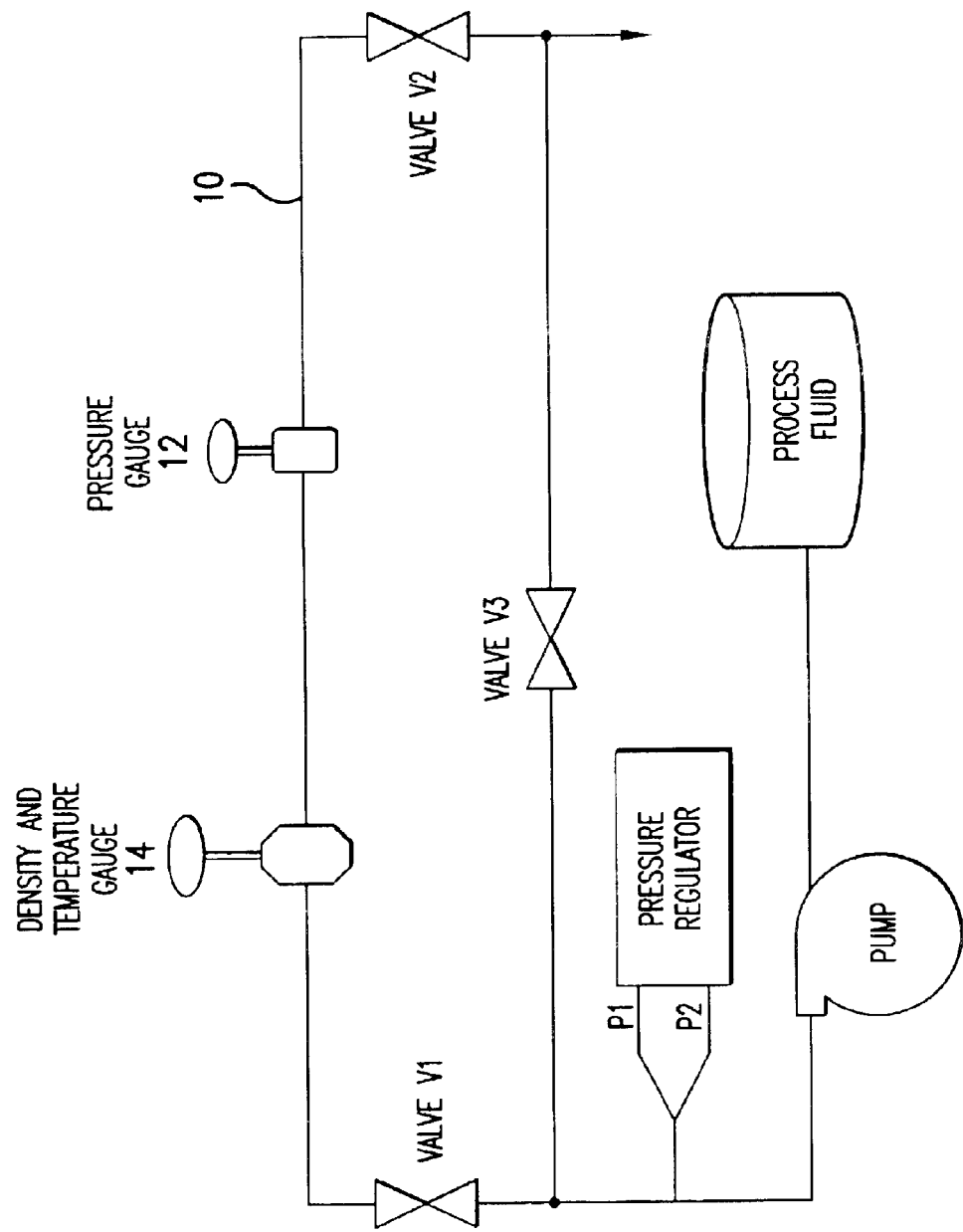
FIG. 4 is a schematic representation of another indirect measurement apparatus embodiment, which measures state conditions of pressure difference, temperature, and change in volume, in terms of reciprocal density difference, at two different equilibrium states.

Apparatus for Indirect Measurement of Entrained and Dissolved Air Content in Liquids at an Equilibrium State FIG. 4 depicts an indirect measurement apparatus embodiment, which measure state conditions of pressure difference and temperature, as well as the change in volume, as determined indirectly in terms of reciprocal density difference, at two different equilibrium states. The apparatus of FIG. 4 takes measurements in a "no flow" state. Apparatus 10 of FIG. 4 includes a reservoir for process fluid, from which the fluid may be pumped by through piping which is under the control of a pressure regulator which is capable of setting at least two different pressures P1 and P2 in the system. The order of measurements can be either P1>P2 or P1<P2. Also, these pressures may be set based on system constraints or testing objectives. The fluid flow in the piping is controlled by three valves V1, V2, and V3. This particular apparatus also includes a pressure gauge 12 and a density and temperature gauge 14.

A measurement procedure is carried out on apparatus 10 as follows. Valves V1 and V2 are opened to permit fluid pumped from the reservoir to fill the piping. Valve V3 is partially closed to ensure that measurement gauges 12 and 14 are filled with the fluid. The pressure regulator is set to P1 and valve V2 is closed to pressurize pressure gauge 12 to P1. Valve V1 is closed. Subsequently, pressure, temperature, and density data at pressure level P1 is collected until there is no longer any change in the data, meaning the state of an equilibrium. Subsequently, pressure, temperature, and density data at pressure level P2 can be collected in the same manner until there is no longer any change in the data. The two sets of stabilized pressure, temperature, and density data may then be used in the processes of the algorithms (31), (32), (24), (28) for entrained/dissolved air determination.

This hardware configuration is normally capable of operating at a static state only. Since a state of equilibrium is an essential requirement, such a configuration needs a relatively longer cycle time for completing a course of measurement. Because of the indirect measurement, its measurement accuracy can be impacted by the uniformity of a gas-liquid mixture. The cost of this hardware configuration is even lower than the one presented in FIG. 3 since only one coriolis meter and one pressure sensor are needed.

Example 4

Figure 5:
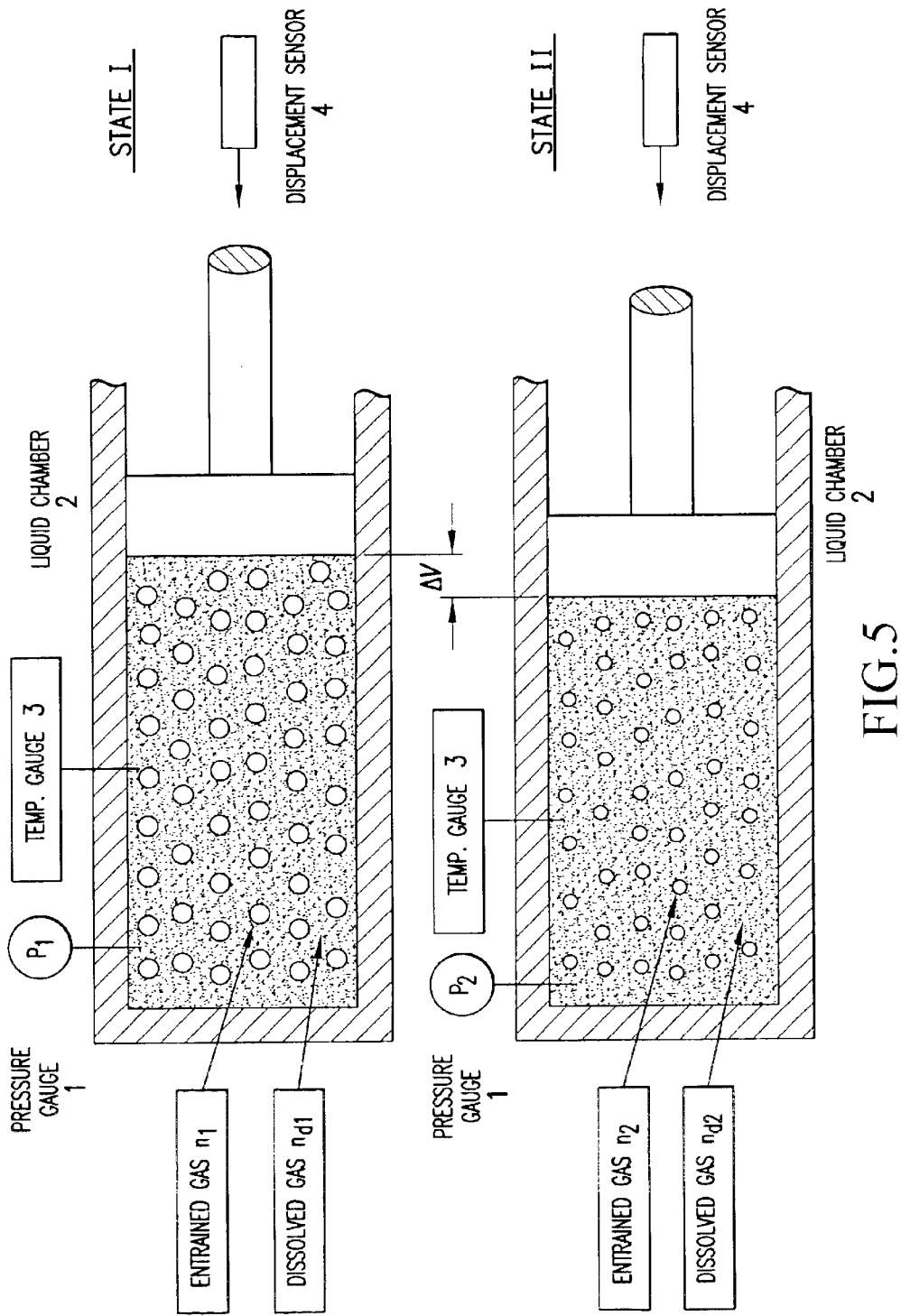
FIG. 5 is a schematic representation of a direct measurement apparatus embodiment of the present invention. This embodiment measures state conditions of pressure difference, temperature, and change in volume, e.g. using a piston cylinder with a liquid chamber as well as a displacement sensor, at two different equilibrium states.

Apparatus for the Direct Measurement of Entrained and Dissolved Air Content in Liquids at an Equilibrium State FIG. 5 represents a direct measurement apparatus embodiment, which measure state conditions of pressure difference, temperature, and change in volume at two different equilibrium states. The apparatus of FIG. 5 also takes measurements in a "no flow" state. The embodiment of FIG. 5 includes cylinder type of apparatus with a liquid chamber 2 for sampling process liquid, in which the volume of the sampled liquid-air mixture is compressible/expandable between two different equilibrium pressures. The order of measurements can be either P1>P2 or P1<P2, with these pressures being set based on system constraints or testing objectives. This particular apparatus also includes a pressure gauge 1, temperature gauge 2, and a displacement sensor 4, which, as familiar to those skilled in the art, is used for determining the change in volume of the liquid chamber at different levels of pressures.

A measurement procedure is carried out on the apparatus as follows. Liquid chamber 2 is opened to permit a sample of liquid-air mixture to fill the chamber. The chamber is closed and pressurized at a preset pressure P1. Subsequently, pressure, temperature, and the volume of liquid chamber at pressure level P1 (State I), in terms of displacement, is collected until there is no longer any change in the data, meaning the state of an equilibrium. Subsequently, pressure, temperature, and volume data at pressure level P2 (State II) can be collected in the same fashion until there is no longer any change in the data. The two sets of stabilized pressure, temperature, and volume data may then be used for determining entrained and dissolved air by applying algorithms (35), (36), (24), and (28).

This hardware configuration is usually capable of operating at a static state only. Since a state of equilibrium is required with this configuration, it also needs a relatively longer cycle time for completing a course of measurement. Because of the change in volume being measured directly, this configuration is capable of tolerating a high-degree of non-uniformity with a gas-liquid mixture. In addition, this configuration has a unique capability to be operated below the atmospheric pressure, which would otherwise be a limitation for the other three configurations. The cost of this hardware configuration can be relatively lower since no coriolis meter is required with this option.

Example 5

Optimizing Deaerator Operations in Coating Processes

Certain coating processing environments require that excessive entrained gases should be removed from the coating liquids prior to distributing the coating liquids onto the substrate. This is because entrained gas bubbles, especially larger ones, deteriorate coating quality and result in coating defects such as intolerable pinholes. Deaeration is therefore highly desirable where excessive entrained gas bubbles are presented. With the rapidly advancing technology of high-speed jet and curtain coating, in which thin liquid sheets are either injected or allowed to fall freely onto a substrate to be coated, any entrained large gas bubbles may even cause the breakdown of the integrity of the free coating liquid sheet. Thus, deaeration is a must for high-speed jet and curtain coating applications.

One application of the present invention, as depicted in FIG. 8 "Entrained air measurement installed in both inlet and outlet of deaerator for quantitative determination of deaeration efficiency", incorporates this invention both before and after the deaerator in a curtain coater piping system. The percent entrained air measurements provided before and after the deaerator unit improve the manufacturing process by enabling optimization of the deaerator unit, based upon determination of its process-specific deaeration efficiency. Process parameter adjustments (degree of vacuum, rotation speed of the deaerator, etc.) are made based upon the differences in "before" and "after" values. The output from the upstream apparatus embodiment is compared to that from the downstream apparatus embodiment to calculate the efficiency of air removal, and process parameters are changed to enhance the amount of air removed by the deaerator unit.

In addition to coating processes, other typical applications for deaerator systems include the packaging of ointments, creams, lotions, toothpaste, mayonnaise, ketchup, and lubricating grease.

Example 6

Quality Control in Coating Application Systems

In Example 5, the deaerator units can be used to minimize waste costs due to the manufacture of off-quality product. When the level of percent entrained air that causes quality defects in a product is known, then the measured percent entrained air can be used to shutdown production, or can be monitored to predict when off-quality production may soon occur. It is not necessary to incorporate two (that is, "before" and "after") apparatus embodiments of this invention into processing systems (as illustrated in FIG. 8). Instead, the system could be configured with a single apparatus embodiment of this invention, located for instance after the deaerator unit, as depicted in FIG. 9. The system can then be configured to set off an alarm if too great a quantity of air bubbles are detected in the slurry downstream of the deaerator unit. With a processing system alarmed in this manner, the amount of expensive defoaming agent can be kept low, but can be immediately increased as soon as the alarm is triggered.

Also, since 100% deaeration is generally impracticable and unnecessary, an accurate measurement of the permissible maximum percent entrained air that the coaters can tolerate without causing noticeable quality problems enables controlling the coaters to run within acceptable operation windows.

As noted above, other typical applications for deaerator system improvements in accordance with this invention include—without limitation—the packaging of ointments, creams, lotions, toothpaste, mayonnaise, ketchup, and lubricating grease.

Example 7

Percent Solids Control in Coating Substrates

One application of this invention is the on-line determination of the true density of a coating slurry applied to a substrate such as a paper web. The true density is then used to predict coating percent solids as described in U.S. Pat. No. 6,496,781 B1, entitled IMPROVED MIXTURE CONCENTRATION CONTROL IN MANUFACTURING PROCESSES, referenced above. This coating percent solids data is then used to more efficiently control the application of the coating slurry onto the paper web. A significant processing benefit is realized due to the fact that percent solids is often the primary coating property affecting the quantity of coating being applied to the paper web. As the accuracy of the measurement of true density is improved, the accuracy of predicted coating slurry percent solids is improved. As the accuracy of coating slurry percent solids is improved, the control of the quantity of the coating slurry is also improved.

Paper coating slurries usually contain at least one and often all three of the following materials: pigments, binders, and additives. Generally, pigments constitute the main component of paper coating slurries. Pigments commonly used in current paper and board applications are kaolin clay, calcium carbonate, titanium dioxide, alumina trihydrate, synthetic and structured pigments, and so on. Binders normally constitute just a small part of paper coating slurries. Besides their role of binding, they also serve to fill up voids in the cellulose/pigment matrix. Natural binders include starch, soy protein, casein, while synthetic binders include styrene-butadiene latex, polyvinyl acetate latex, vinyl acrylic latex, polyvinyl alcohol, and so on. Although coating additives constitute only a small percent of paper coating slurries, they form a large, complex group with each serving a particular function. Coating additives include dispersants, viscosity modifier or water-holding agents, lubricants, crosslinkers or insolubilizers, biocides, pH control agents, repellents, optical brighteners, dyes, and foam control agents. This invention enables improved management of processes for applying any combinations of such materials.

Specifically, for a production environment in which the following production information is available to an on-line control system—1) the dry coating component ratio, 2) the relationship between the Additive Volume Coefficient of each coating component and the concentration of the component in the mixture, 3) the true density of each coating solid or solute component, and 4) the true density as determined in accordance with this invention—the following calculations are employed within the control system to determine the coating slurry percent solids:

Determine the true density of the coating slurry by means of the technique provided by the present invention;

Using that true density determination, estimate (more accurately) the coating slurry percent solids by the method described in U.S. Pat. No. 6,496,781 B1; and Employ the (more accurate) coating slurry percent solids estimate to optimize coater operations.

Broadly speaking, this specific embodiment of the present invention provides a method of monitoring a continuous coating of a substrate with solids delivered in a slurry of water. A first step in the present application comprises setting a target solids weight-% for the slurry. That is, in order to practice the present invention, one must determine what the solids weight-% in the coating slurry should be in order to provide a coated substrate having the desired properties. Having determined that target solids weight-%, one proceeds to provide a continuous industrial coating line with appropriate volumes of water and with appropriate amounts of the solid or solids with which it is desired to coat the substrate.

In order to implement the present invention, one may modify a conventional industrial coating line by inserting an apparatus embodiment of the present invention into it. Referring to FIG. 6, industrial coating line 1 comprises coating run tank 4, pump 5, and coating slurry bath 14. These elements are linked by piping 7. A roll 8 is partially immersed in bath 14, and substrate 9 travels around the roll through the bath where it contacts coating slurry 13 (which includes a liquid carrier component). An apparatus embodiment of the present invention 6, along with the composition of the coating slurry, are fed as inputs into distributed control system 10. In accordance with the present invention, the distributed control system 10 converts these inputs to the true density of the coating. This true density is then converted into solids weight-% of the coating, making use of the procedure described in U.S. Pat. No. 6,496,781 B1, referenced above. This actual solids weight-% determination, in turn, is compared to the target coating solids weight-% for the slurry. If there is a difference, the distributed control system 10 adjusts coating inflows 2 and 3 with flow control valves 11 and 12 as appropriate to correct this difference.

This Example represents use in one particular paper coating process. However, those skilled in the art will realize that this invention can be applied similarly to virtually any other commercial coating methods and in any other process environments where information on true liquid density or % solids is desirable.

Example 8

Improved Control of Syrup Makedown (True Liquid Density)

Another application of this invention is the on-line determination of the concentration of sugars dissolved in water, commonly referred to as ∘Brix. This measurement is used to control the process of making syrup such as that used with canned fruit. Such a control provides the food manufacturer with the ability to control the product's sugar content. This provides the customer with a consistent taste over time, and/or the knowledge of a sugar content maximum, which is important to those with certain health conditions.

Current methods of measuring ∘Brix include converting the measurement of syrup density to ∘Brix. This can be done using long-standing conversion tables available in the public domain. When incorporated into a control system, these conversions can occur on-line, thus providing real-time ∘Brix measurement. However, the accuracy of the density measurement is often unsatisfactory due to the presence of air entrained in the syrup being measured. In such a case, incorporating an apparatus of embodying the present invention into a syrup piping system, as shown in FIG. 7, provides more accurate control of the finished product than can be achieved in the absence of this invention.

When used in conjunction with an on-line control system as described in Example 4, the present invention provides a method for accurately converting density to ∘Brix by supplying measured density values having improved accuracy. The first step in this application comprises setting a target ∘Brix for the dilute syrup. Next, the flows of concentrated syrup and dilution water are controlled to maintain the dilute syrup at the targeted ∘Brix.

Referring to FIG. 7, concentrated syrups 31, 32, and 33 are blended together as a concentrated mixture 4 in a ratio controlled by flow valves 43. The concentrated mixture travels through pump 35 to mixing tee 36 where it is blended with water from supply header 40. This dilute mixture travels through static mixer 38 to an apparatus embodiment of the present invention 39. The distributed control system 41 then converts the inputs to ∘Brix, making use of the air-free true densities of the dilute syrup provided by the application of this invention. This, in turn, is compared to the target ∘Brix. If a difference exists, the distributed control system adjusts the flow control valves 33 and 34 to correct the discrepancy.

Example 9

Precise Control of Carbonation Level in Beverages

Still another application of this invention is a process for preparing a carbonated beverage. In this Example, a quantitative target for a concentration of carbon dioxide, to be blended into an aqueous medium comprising water, high fructose corn syrup, caramel color, phosphoric acid, natural flavors, and caffeine, is set. Then carbon dioxide is supplied to the aqueous medium in a vessel, and these components are mixed to form a carbonated aqueous medium in the vessel. As this process is being carried out, the total carbon dioxide concentration is determined by procedures set forth hereinabove. This calculated carbon dioxide concentration is compared to the target carbon dioxide concentration. When the calculated carbon dioxide concentration is greater than or less than the target carbon dioxide concentration, the volume of carbon dioxide being supplied to the aqueous medium is lowered or raised, respectively.

In this type of application of the present invention, it is necessary to collect data at pressures lower enough than that corresponding to the target carbon dioxide concentration to cause some carbon dioxide to come out of solution. This is because all of the carbon dioxide is in the dissolved state at the target pressure, while the present invention requires the presence of entrained gases to be effective. The Direct Measurement Method is capable of operating at any pressure, including pressures below the atmospheric pressure. The algorithms (34)–(37), (24), and (28) are suitable for the corresponding calculation.

Example 10

Improved Water Cut Determination of the Outflow at a Hydrocarbon Well Site

Yet another application of this invention is the in-line measurement of the mass fraction of water (Water Cut) of the outflow from hydrocarbon wells. This application, using the embodiment as depicted in FIG. 2, requires the measurement of fluid apparent density at each of two pressure states, as well as measurements of the temperature and pressure at which these densities were measured. These two sets of pressure, temperature, and density data may then be used in the processes of the algorithms (22)–(24) and (28) for entrained/dissolved natural gas calculation, which are described in detail in Example 1. The measurement of the two sets of data and consequent determination of entrained/dissolved natural gas could also be accomplished by employing the embodiments/algorithms as illustrated in Example 2, or 3, or 4, respectively. Additionally, this application requires that the individual densities of the water-phase and oil-phase be supplied via alternative means. As an example, these individual phase densities could be tested in a laboratory from samples drawn at the well site. As an alternative example, these densities could be measured by in-line instrumentation, of which this invention is an example, at a point downstream that occurs after the water-phase and oil-phase are separated. A distributed control system then converts these inputs of water-phase density, oil-phase density, and true density of the mixture to Water Cut of the mixture. This is accomplished with the simple relationship:

$$WaterCut = \frac{WaterPhaseDensity(OilPhaseDensity - TrueDensityofMixtre)}{TrueDensityofMixture(OilPhaseDensity - WaterPhaseDensity)}$$

which applies to volumetrically additive components such as oil and water.

The invention being thus described, it will be evident that the same may be varied in many ways. Such variations are not to be regarded as a departure from the spirit and scope of the invention, and all such modifications as would be apparent to one skilled in the art likewise constitute a part of the present invention.

What is claimed is:

1. A method for automatically controlling the output of a continuous process with a liquid carrier that contains one or more gases, the method comprising the steps of:
   a.) setting a quantitative target for volume-% of one or more gases in the liquid carrier;
   b.) calculating the volume percentage of said gas in said liquid sample by using equation (28)

$$x\% = \frac{V_s}{V_s + V} \tag{28}$$

wherein V is the volume of the gas-free liquid calculated by equation (23)

$$V = \frac{1}{\rho_1} - \left[\frac{P_2}{P_2 - P_1}\left(\frac{1}{\rho_1} - \frac{1}{\rho_2}\right) - \frac{RT}{P_2 - P_1}g\left(\frac{\Delta P}{Q^a}\right)\right] \tag{23}$$

in which $P_1$ and $P_2$ are two different ambient pressures and $\Delta P = P_2 - P_1$, $\rho_1$ and $\rho_2$ are apparent densities of the liquid sample measured at $P_1$ and $P_2$, respectively, R is the constant of the Ideal Gas Law, T is the liquid temperature, Q is the flow rate, and $g(\Delta P/Q^a)$ is a function through which the gas solubility coefficients at a dynamic state are determined; and $V_s$ is determined by equation (27)

$$V_s = \frac{T_s}{T}\frac{P_1 P_2}{P_s(P_2 - P_1)}\left(\frac{1}{\rho_1} - \frac{1}{\rho_2}\right) - \frac{RT_s}{P_s}\left(\frac{P_1}{P_2 - P_1}g\left(\frac{\Delta P}{Q^a}\right) - g\left(\frac{P_1 - P_s}{Q^a}\right)\right). \tag{27}$$

in which $P_s$ and $T_s$ are standard pressure (1 atm) and temperature (0° C.), $P_1$, $P_2$, $P_s$, $\Delta P$, $\rho_1$, $\rho_2$, R, Q, and T are the same as defined in this claim, and $$g\left(\frac{P_1 - P_s}{Q^a}\right)$$

is a function for determining the amount of gas being dissolved between $P_1$ and $P_s$;
   c.) comparing the calculated volume-% gas to the target volume-% gas; and,
   d.) if the calculated volume-% gas in the liquid carrier is greater or less than the target volume-% gas, lowering or raising the amount of gas in the liquid carrier.

2. A method for controlling the output of processing a liquid as mixture in a batch mode, the method comprising the steps of:
   a.) setting a quantitative target for volume-% of one or more gases in the mixture;
   b.) subjecting the mixture to two different pressure states and measuring the apparent density of the mixture at each of the two pressure states;
   c.) calculating the volume percentage of said gas in said liquid sample by using equation (28)

$$x\% = \frac{V_s}{V_s + V} \tag{28}$$

wherein $V_s$ is determined by equation (33)

$$V_s = \frac{T_s}{T}\frac{P_1 P_2}{P_s(P_2 - P_1)}\left(\frac{1}{\rho_1} - \frac{1}{\rho_2}\right) - \frac{RT_s}{C} \tag{33}$$

in which $P_1$ and $P_2$ are two different ambient pressures, $\rho_1$ and $\rho_2$ are apparent densities of the liquid sample measured at $P_1$ and $P_2$, respectively, $P_s$ and $T_s$ are standard pressure (1 atm) and temperature (0° C.), R is the constant of the Ideal Gas Law, T is the temperature of the liquid sample, and C is the gas solubility coefficient at a static state; and V is the volume of the gas-free liquid calculated through equation (32)

$$V = \frac{1}{\rho_1} - \left[\frac{P_2}{P_2 - P_1}\left(\frac{1}{\rho_1} - \frac{1}{\rho_2}\right) - \frac{RT}{C}\right] \tag{32}$$

in which T is the liquid temperature, and $P_1$, $P_2$, $\rho_1$, $\rho_2$, and R are the same as defined in this claim,
   d.) comparing the calculated volume-% gas to the target volume-% gas; and,
   e.) if the calculated volume-% gas in the liquid carrier component is greater or less than the target volume-% gas, lowering or raising the amount of gas mixed in the liquid.

3. A method for automatically controlling the output of a continuous process that requires mixing of a solid or liquid component with a liquid carrier component, the method comprising the steps of:
   a.) setting a quantitative target for weight-% in the liquid carrier component of one or more solids and/or for concentration of one or more liquids in the liquid carrier component;
   b.) continuously mixing said solids and/or liquids with the liquid carrier component;
   c.) determining the true density, $\rho$, by employing equation (24)

$$\rho = \frac{1}{V} \tag{24}$$

wherein the volume, V, is calculated from equation (23)

$$V = \frac{1}{\rho_1} - \left[\frac{P_2}{P_2 - P_1}\left(\frac{1}{\rho_1} - \frac{1}{\rho_2}\right) - \frac{RT}{P_2 - P_1}g\left(\frac{\Delta P}{Q^a}\right)\right] \tag{23}$$

in which $P_1$ and $P_2$ are two different ambient pressures and $\Delta P = P_2 - P_1$, $\rho_1$ and $\rho_2$ are apparent densities of the liquid sample measured at $P_1$ and $P_2$, respectively, R is the constant of the Ideal Gas Law, T is the temperature of the liquid sample, Q is the flow rate, and $g(\Delta P/Q^a)$ is a function through which the gas solubility coefficients at a dynamic state are determined;

d.) calculating the weight-% of solids and/or the liquid concentration in the mixture from the true density ρ so determined;

e.) comparing the calculated weight-% solids or concentration to the target weight-% solids or concentration; and, f.) if the calculated weight-% solids or concentration is greater or less than the target weight-% solids or concentration, lowering or raising the amount of solids or liquids mixed in step b.).

4. The method of claim 3 for continuously coating a substrate, which method comprises:

a.) setting a quantitative target for weight-% of one or more solids to be coated onto a substrate;

b.) continuously applying the solids to the substrate via a carrier fluid;

c.) measuring the apparent density of the slurry;

d.) determining the true density of the slurry;

e.) calculating the weight-% of solids in the slurry in the manner recited in claim 3;

f.) comparing the calculated weight-% solids to the target weight-% solids; and, g.) if the calculated weight-% is greater or less than the target weight-%, lowering or raising the amount of solids applied in step b.).

5. The method of claim 4, in which the substrate is a paper web and the solids component comprises kaolin clay, calcium carbonate, titanium dioxide, or alumina trihydrate.

6. The method of claim 3 for controlling the output of a continuous process for preparing a syrup, which method comprises:

a.) setting a quantitative target for a concentration of one or more carbohydrates and/or carbohydrate-containing liquids to be blended into a syrup;

b.) continuously supplying the carbohydrate and/or carbohydrate-containing liquid and a dilution liquid to a vessel and mixing said liquids to form a slurry;

c.) measuring the apparent density of the slurry;

d.) determining the true density of the slurry;

e.) converting this true density to the calculated carbohydrate concentration;

f.) comparing the calculated carbohydrate concentration to the target carbohydrate concentration; and, g.) if the calculated carbohydrate concentration is greater or less than the target carbohydrate concentration, lowering or raising the amount of carbohydrates and/or volume of carbohydrate-containing liquids supplied in step b.).

7. The method of claim 4, in which carbohydrates comprising sucrose and carbohydrate-containing liquids comprising corn syrup and high fructose corn syrup are mixed with a dilution liquid comprising water.

8. An indirect method of determining the amount of gas entrained in a liquid in a batch mode, the method comprising the steps of:

subjecting a mixture of an incompressible liquid sample and a compressible gas to two different pressure states, measuring the temperature and apparent density of the mixture at each of the two pressure states, and calculating the volume percentage of said gas in said liquid sample by using equation (28)

$$x\% = \frac{V_s}{V_s + V} \quad (28)$$

wherein $V_s$ is determined by equation (33)

$$V_s = \frac{T_s}{T} \frac{P_1 P_2}{P_s(P_2 - P_1)}\left(\frac{1}{\rho_1} - \frac{1}{\rho_2}\right) - \frac{RT_s}{C} \quad [33]$$

in which $P_1$ and $P_2$ are two different ambient pressures, $\rho_1$ and $\rho_2$ are apparent densities of the liquid sample measured at $P_1$ and $P_2$, respectively, $P_s$ and $T_s$ are standard pressure (1 atm) and temperature (0° C.), R is the constant of the Ideal Gas Law, T is the temperature of the liquid sample, and C is the gas solubility coefficient at a static state; and V is the volume of the gas-free liquid calculated through equation (32)

$$V = \frac{1}{\rho_1} - \left[\frac{P_2}{P_2 - P_1}\left(\frac{1}{\rho_1} - \frac{1}{\rho_2}\right) - \frac{RT}{C}\right]. \quad [32]$$

9. An indirect method of continuously determining the amount of gas entrained in a liquid, the method comprising the steps of:

continuously measuring the temperature, flow rate, and apparent density of the mixture at two different pressure states, and calculating the volume percentage of said gas in said liquid by using equation (28)

$$x\% = \frac{V_s}{V_s + V} \quad (28)$$

wherein V is the volume of the gas-free liquid calculated by equation (23)

$$V = \frac{1}{\rho_1} - \left[\frac{P_2}{P_2 - P_1}\left(\frac{1}{\rho_1} - \frac{1}{\rho_2}\right) - \frac{RT}{P_2 - P_1}g\left(\frac{\Delta P}{Q^a}\right)\right] \quad (23)$$

in which $P_1$ and $P_2$ are two different ambient pressures and $\Delta P = P_2 - P_1$, $\rho_1$ and $\rho_2$ are apparent densities of the liquid sample measured at $P_1$ and $P_2$, respectively, R is the constant of the Ideal Gas Law, T is the liquid temperature, Q is the flow rate, $g(\Delta P/Q^a)$ is a function for determining the amount of gas being dissolved between $P_2$ and $P_1$, and $V_S$ is determined by equation (27)

$$V_s = \frac{T_s}{T} \frac{P_1 P_2}{P_s(P_2 - P_1)}\left(\frac{1}{\rho_1} - \frac{1}{\rho_2}\right) - \frac{RT_s}{P_s}\left(\frac{P_1}{P_2 - P_1}g\left(\frac{\Delta P}{Q^a}\right) - g\left(\frac{P_1 - P_s}{Q^a}\right)\right). \quad (27)$$

in which $P_s$ and $T_s$ are standard pressure (1 atm) and temperature (0° C.), and $$g\left(\frac{P_1 - P_s}{Q^a}\right)$$

is a function for determining the amount of gas being dissolved between $P_1$ and $P_s$.

10. An indirect method of determining the air-free density of a liquid at a static state, the method comprising the steps of:

subjecting a mixture of an incompressible liquid sample and a compressible gas to two different pressure states, measuring the temperature and apparent density of the mixture at each of the two pressure states, and calculating the true density of said liquid sample by using equation (24)

$$\rho = \frac{1}{V} \quad (24)$$

wherein V is the volume of the gas-free liquid as determined by equation (32)

$$V = \frac{1}{\rho_1} - \left[\frac{P_2}{P_2 - P_1}\left(\frac{1}{\rho_1} - \frac{1}{\rho_2}\right) - \frac{RT}{C}\right] \quad [32]$$

in which $P_1$ and $P_2$ are two different ambient pressures, $\rho_1$ and $\rho_2$ are apparent densities of the liquid sample measured at $P_1$ and $P_2$, respectively, R is the constant of the Ideal Gas Law, T is the temperature of the liquid sample, and C is the gas solubility coefficient at a static state.

11. An indirect method of determining the gas-free density of a gas-liquid mixture at a dynamic state, the method comprising the steps of:

measuring two different apparent densities of the mixture and two corresponding ambient pressures at which the apparent densities are determined, measuring the temperature and flow rate, and calculating the true density of said liquid sample by using equation (24)

$$\rho = \frac{1}{V} \quad (24)$$

wherein V is the volume of the gas-free liquid as determined by equation (23)

$$V = \frac{1}{\rho_1} - \left[\frac{P_2}{P_2 - P_1}\left(\frac{1}{\rho_1} - \frac{1}{\rho_2}\right) - \frac{RT}{P_2 - P_1} g\left(\frac{\Delta P}{Q^a}\right)\right] \quad [23]$$

in which $P_1$ and $P_2$ are two different ambient pressures and $\Delta P = P_2 - P_1$, $\rho_1$ and $\rho_2$ are apparent densities of the liquid sample measured at $P_1$ and $P_2$, respectively, R is the constant of the Ideal Gas Law, T is the temperature of the liquid sample, and $$g\left(\frac{\Delta P}{Q^a}\right)$$

is the gas solubility function.

12. An indirect method for determining gas solubility coefficients for a gas-liquid mixture at a dynamic state, the method comprising the steps of:

a.) subjecting the said gas-liquid mixture to flow at several different flowrates, $Q_1, Q_2, \ldots, Q_i$;

b.) measuring two different apparent densities of the mixture and two related ambient pressures at which the apparent densities are determined at each of the flow rates;

c.) acquiring off-line the true, gas-free liquid density, $\rho^*$, through one-time measurement;

d.) determining the gas solubility coefficients, $A_0$, $A_1$, $A_2$, ..., $A_i$, by solving a group of linear equations (19)

$$A_0 + A_1\left(\frac{\Delta P}{Q^a}\right) + A_2\left(\frac{\Delta P}{Q^a}\right)^2 + \cdots + A_i\left(\frac{\Delta P}{Q^a}\right)^i = S_1 \bigg|_{Q=Q_1} \quad (19)$$

$$A_0 + A_1\left(\frac{\Delta P}{Q^a}\right) + A_2\left(\frac{\Delta P}{Q^a}\right)^2 + \cdots + A_i\left(\frac{\Delta P}{Q^a}\right)^i = S_2 \bigg|_{Q=Q_2}$$

$$A_0 + A_1\left(\frac{\Delta P}{Q^a}\right) + A_2\left(\frac{\Delta P}{Q^a}\right)^2 + \cdots + A_i\left(\frac{\Delta P}{Q^a}\right)^i = S_i \bigg|_{Q=Q_i}$$

in which $Q_1, Q_2, \ldots, Q_i$, are the different flow rates generated for obtaining the gas solubility coefficients at a dynamic state, $\Delta P$ is the difference of the said two ambient pressures at each of the flow rates, a is an index reflecting the weak influence of flow rate on gas solubility, and $S_1, S_2, \ldots, S_i$ are intermediate variables determined by equation (20)

$$S_1 = \frac{1}{RT}\left[P_I\left(\frac{1}{\rho_I} - \frac{1}{\rho^*}\right) - P_{II}\left(\frac{1}{\rho_{II}} - \frac{1}{\rho^*}\right)\right]\bigg|_{Q=Q_1} \quad (20)$$

$$S_2 = \frac{1}{RT}\left[P_I\left(\frac{1}{\rho_I} - \frac{1}{\rho^*}\right) - P_{II}\left(\frac{1}{\rho_{II}} - \frac{1}{\rho^*}\right)\right]\bigg|_{Q=Q_2}$$

$$\ldots$$

$$S_i = \frac{1}{RT}\left[P_I\left(\frac{1}{\rho_I} - \frac{1}{\rho^*}\right) - P_{II}\left(\frac{1}{\rho_{II}} - \frac{1}{\rho^*}\right)\right]\bigg|_{Q=Q_i}$$

in which $P_I$ and $P_{II}$ are two different ambient pressures measured at each of the flow rates, $\rho_I$ and $\rho_{II}$ are apparent densities of the gas-liquid mixture measured at $P_I$ and $P_{II}$, respectively, R is the constant of the Ideal Gas Law, T is the liquid temperature, Q is the flow rate, and $\rho^*$ is the predetermined gas-free liquid density as defined in c.);

e.) attaining the gas solubility function $$g\left(\frac{\Delta P}{Q^a}\right) = A_0 + A_1\left(\frac{\Delta P}{Q^a}\right) + A_2\left(\frac{\Delta P}{Q^a}\right)^2 + \ldots + A_i\left(\frac{\Delta P}{Q^a}\right)^i$$

upon the solution of the gas solubility coefficients, $A_0$, $A_1$, $A_2$, $A_i$.

13. An indirect method for determining the gas solubility coefficient for a gas-liquid mixture at a static state, the method comprising the steps of:

a.) measuring two different apparent densities of the mixture and two related ambient pressures at which the apparent densities are determined;

b.) acquiring off-line the true, gas-free liquid density, $\rho^*$, through one-time measurement;

c) determining the gas solubility coefficients, C, at a static state by solving equation (30)

$$C = RT(P_{II} - P_I)\left[P_I\left(\frac{1}{\rho_I} - \frac{1}{\rho^*}\right) - P_{II}\left(\frac{1}{\rho_{II}} - \frac{1}{\rho^*}\right)\right]^{-1} \quad (30)$$

in which $P_I$ and $P_{II}$ are two different ambient pressures, $\rho_I$ and $\rho_{II}$ are apparent densities of the gas-liquid mixture measured at $P_I$ and $P_{II}$, respectively, R is the constant of the Ideal Gas Law, T is the liquid temperature, and $\rho^*$ is the predetermined gas-free liquid density as defined in b.).

14. The method of one of claims 8–13, wherein said two pressure states differ from one another by at least 1 psi, preferably by at least 1 atmosphere.

15. The method of one of claims 8–13, wherein said two pressure states differ from one another at least to the extent that the two different apparent densities of said liquid differ from one another by at least 0.2%, preferably by at least 0.5%.

16. A direct method of determining the amount of gas entrained in a liquid, the method comprising the steps of:
   subjecting a mixture of an incompressible liquid sample and a compressible gas to two different pressure states,
   measuring the temperature and volume of the mixture at each of the two pressure states,
   determining the changes in volume of the mixture between the two pressure states, and
   calculating the volume percentage of said gas in said liquid sample by using equation (28)

$$x\% = \frac{V_s}{V_s + V} \tag{28}$$

wherein $V_s$ is determined by equation (37)

$$V_s = \frac{T_s}{T} \frac{P_1 P_2 \Delta V}{P_s(P_2 - P_1)} - \frac{RT_s}{C} \tag{37}$$

in which $T_s$ is 0° C., $P_1$ and $P_2$ are two different ambient pressures, $\Delta V$ is the volume difference of the gas-liquid mixture in a sample chamber between $P_1$ and $P_2$, R is the constant of the Ideal Gas Law, T is the temperature of the liquid sample, $P_s$ is 1 atm, and C is the gas solubility coefficient at a static state; and V is the volume of the gas-free liquid in the sample chamber determined by equation (36)

$$V = V_{t1} - \left[\frac{P_2 \Delta V}{P_2 - P_1} - \frac{RT}{C}\right] \tag{36}$$

in which $V_{t1}$ is the volume of the gas-liquid mixture in the sample chamber at $P_1$.

17. A direct method of determining the air-free density of a liquid, the method comprising the steps of:
   subjecting a mixture of an incompressible liquid sample and a compressible gas to two different pressure states,
   measuring the temperature and volume of the mixture at each of the two pressure states,
   determining the changes in volume of the mixture between the two pressure states, and
   calculating the true density of said liquid sample by using equation (24)

$$\rho = \frac{1}{V} \tag{24}$$

wherein V is the volume of the gas-free liquid as determined by equation (36)

$$V = V_{t1} - \left[\frac{P_2 \Delta V}{P_2 - P_1} - \frac{RT}{C}\right] \tag{36}$$

in which $P_1$ and $P_2$ are two different ambient pressures, $V_{t1}$ is the volume of gas-liquid mixture in the sample chamber at $P_1$, $\Delta V$ is the change in volume of gas-liquid mixture in the sample chamber between $P_1$ and $P_2$, R is the constant of the Ideal Gas Law, T is the temperature of the liquid sample, and C is the gas solubility coefficient at a static state.

18. A direct method for determining the gas solubility coefficient for a gas-liquid mixture at a static state, the method comprising the steps of:

a.) subjecting a mixture of an incompressible liquid sample and a compressible gas to a sample chamber;
b.) compressing or expanding the sample chamber and measuring the volume of gas-liquid mixture, $V_{t1}$, at the first pressure state, $P_I$;
c.) compressing or expanding the sample chamber further and measuring the volume of gas-liquid mixture, $V_{tII}$, at the second pressure state, $P_{II}$;
d.) increasing the pressure of the sample chamber excessively to dissolve all of the free gas and measuring the volume of gas-free liquid in the sample chamber, V;
e.) calculating the volumes of the free gas, $V_I$ and $V_{II}$ at $P_I$ and $P_{II}$, respectively, $V_I = V_{tI} - V$ and $V_{II} = V_{tII} - V$;
f.) determining the gas solubility coefficient, C, by using equation (34)

$$C = \frac{RT(P_{II} - P_I)}{P_I V_I - P_{II} V_{II}} \tag{34}$$

in which $P_I$ and $P_{II}$ are two different ambient pressures, $V_I$ and $V_{II}$ are volumes of the gas-liquid mixture in the sample chamber measured at $P_I$ and $P_{II}$, respectively, R is the constant of the Ideal Gas Law, T is the liquid temperature.

19. The method of claim 18, in which the volume of gas-free liquid in the sample chamber, V is determined with degassing chemicals or by allowing the sample to sit for a sufficiently long time to dissipate all of the free gas bubbles, rather than by the procedure of step d.).

20. The method of one of claims 16–19, wherein said two pressure states differ from one another at least to the extent that the two different volumes differ from one another by at least 0.2%, preferably by at least 0.5%.

21. The method of one of claims 16–19, wherein said two pressure states differ from one another by at least 1 psi, preferably by at least 1 atmosphere.

22. A method for controlling the output of a process with a liquid carrier that contains one or more gases, the method comprising the steps of:
   a.) setting a quantitative target for volume-% of one or more gases in the liquid carrier;
   b.) calculating the volume percentage of said gas in said liquid sample by using equation (28)

$$x\% = \frac{V_s}{V_s + V} \tag{28}$$

wherein $V_s$ is determined by equation (37)

$$V_s = \frac{T_s}{T} \frac{P_1 P_2 \Delta V}{P_s(P_2 - P_1)} - \frac{RT_s}{C} \tag{37}$$

in which $T_s$ is 0° C., $P_1$ and $P_2$ are two different ambient pressures, $\Delta V$ is the volume difference of the free gas between $P_1$ and $P_2$, R is the constant of the Ideal Gas Law, T is the temperature of the liquid sample, $P_s$ is 1 atm, and C is the gas solubility coefficient at a static state; and V is the volume of the gas-free liquid in the sample chamber determined by equation (36)

$$V = V_{t1} - \left[\frac{P_2 \Delta V}{P_2 - P_1} - \frac{RT}{C}\right] \tag{36}$$

in which $V_{t1}$, is the volume of the gas-liquid mixture in the sample chamber at $P_1$, and $P_1$, $P_2$, $P_s$, $\Delta V$, R, and C are the same as being defined in this claim;

c.) comparing the calculated volume-% gas to the target volume-% gas; and, d.) if the calculated volume-% gas in the liquid carrier is greater or less than the target volume-% gas, lowering or raising the amount of gas in the liquid carrier.

23. A method for controlling the output of a process for preparing a carbonated beverage, which method comprises:

a.) setting a quantitative target for a concentration of carbon dioxide to be blended into an aqueous medium;

b.) supplying carbon dioxide to the aqueous medium in a vessel and mixing those components to form a carbonated aqueous medium in the vessel at a preset "bottling" pressure $P_0$, wherein $P_0$ is the produced "bottling" pressure inside a sealed carbonated beverage container, at which pressure all of the free carbon dioxide is dissolved into the aqueous medium;

c.) diverting a carbonated aqueous medium sample from the vessel into a sample measurement chamber at the same "bottling" pressure $P_0$;

d.) reducing the aqueous medium pressure from $P_0$ to $P_1$ allowing the dissolved carbon dioxide to start to be released back to the aqueous medium in a free-bubble form while the volume of the sample measurement chamber to be expanded correspondingly;

e.) reducing the aqueous medium pressure further from $P_1$ to $P_2$ allowing more dissolved carbon dioxide to be released back to the aqueous medium in a free-bubble form while the volume of the measurement chamber to be expanded further;

f.) measuring the change in volume of the carbon dioxide liquid mixture between $P_1$ and $P_2$;

g.) determining the volume of free carbon dioxide, $V_s$, in the carbonated aqueous medium at the standard condition using equation (37)

$$V_s = \frac{T_s}{T} \frac{P_1 P_2}{P_s(P_2 - P_1)} \Delta V - \frac{RT_s}{C} \qquad (37)$$

in which $P_1$ and $P_2$ are two different ambient pressures, $\Delta V$ is the change in sample volume between $P_1$ and $P_2$, $P_s$ and $T_s$ are standard pressure and temperature, T is the temperature of the liquid sample, C is the gas solubility coefficient at a static state, and R is the constant of the Ideal Gas Law;

h.) calculating the carbon dioxide concentration using equation (28)

$$x\% = \frac{V_s}{V_s + V} \qquad (28)$$

wherein $V_s$ is the volume of free carbon dioxide determined in step g.) and V is the volume of carbonated aqueous medium in the sample chamber at a preset "bottling" pressure $P_0$ upon which no free bubble should present;

i.) comparing the calculated carbon dioxide concentration to the target carbon dioxide concentration; and, j.) if the calculated carbon dioxide concentration is greater or less than the target carbon dioxide concentration, lowering or raising the volume of carbon dioxide supplied.

24. A method for controlling the output of a process for preparing a carbonated beverage, which method comprises:

a.) setting a quantitative target for a concentration of carbon dioxide to be blended into an aqueous medium;

b.) supplying carbon dioxide to the aqueous medium in a vessel and mixing those components to form a carbonated aqueous medium in the vessel;

c.) diverting a carbonated aqueous medium sample from the vessel into a sample measurement chamber at the first pressure state, $P_1$, with the presence of free carbon dioxide bubbles in the aqueous medium;

d.) reducing the aqueous medium pressure to the second pressure state, $P_2$, allowing more dissolved carbon dioxide to be released back to the aqueous medium in a free-bubble form while the volume of the measurement chamber to be expanded correspondingly;

e.) measuring the change in volume of the carbon dioxide liquid mixture between $P_1$ and $P_2$;

f.) determining the volume of free carbon dioxide, $V_s$, in the carbonated aqueous medium at the standard condition using equation (37)

$$V_s = \frac{T_s}{T} \frac{P_1 P_2}{P_s(P_2 - P_1)} \Delta V - \frac{RT_s}{C} \qquad (37)$$

in which $P_1$ and $P_2$ are two different ambient pressures, $\Delta V$ is the change in sample volume between $P_1$ and $P_2$, $P_s$ and $T_s$ are standard pressure and temperature, T is the temperature of the liquid sample, C is the gas solubility coefficient at a static state, and R is the constant of the Ideal Gas Law;

g.) determining the volume of aqueous medium, V, in which no free carbon dioxide bubble is present, by equation (36)

$$V = V_{t1} - \left[\frac{P_2 \Delta V}{P_2 - P_1} - \frac{RT}{C}\right] \qquad (36)$$

in which $V_{t1}$ is the volume of gas-liquid mixture in the sample chamber at $P_1$;

h.) calculating the carbon dioxide concentration using equation (28)

$$x\% = \frac{V_s}{V_s + V} \qquad (28)$$

wherein $V_s$ is the volume of free carbon dioxide determined in step f.) and V is the volume of aqueous medium, in which no free carbon dioxide bubble is present, as defined in step g.);

i.) comparing the calculated carbon dioxide concentration to the target carbon dioxide concentration; and, j.) if the calculated carbon dioxide concentration is greater or less than the target carbon dioxide concentration, lowering or raising the volume of carbon dioxide supplied.

* * * * *